(12) United States Patent  (10) Patent No.: US 8,311,775 B2
Tsutsui  (45) Date of Patent: Nov. 13, 2012

(54) DEFECT REPAIR APPARATUS AND DEFECT REPAIR METHOD

(75) Inventor: Akiko Tsutsui, Kanagawa (JP)

(73) Assignee: Sony Corporation, Tokyo (JP)

( * ) Notice: Subject to any disclaimer, the term of this patent is extended or adjusted under 35 U.S.C. 154(b) by 444 days.

(21) Appl. No.: 12/603,076

(22) Filed: Oct. 21, 2009

(65) Prior Publication Data

US 2010/0100356 A1    Apr. 22, 2010

(30) Foreign Application Priority Data

Oct. 22, 2008   (JP) ................................. 2008-272528

(51) Int. Cl.
*G06F 11/30* (2006.01)

(52) U.S. Cl. ....................................... 702/184; 702/189

(58) Field of Classification Search .................. 714/100; 702/184, 189; 382/141, 145, 149; 324/500, 324/537
See application file for complete search history.

(56) References Cited

U.S. PATENT DOCUMENTS

| 5,459,410 | A  | * | 10/1995 | Henley .................... 324/760.02 |
| 7,761,182 | B2 | * | 7/2010  | Gallarda et al. ............... 700/121 |
| 7,824,930 | B2 | * | 11/2010 | Koshiishi et al. ............... 438/14 |

FOREIGN PATENT DOCUMENTS

| JP | 2005-221974 | 8/2005 |
| JP | 2008-159930 | 7/2008 |

* cited by examiner

*Primary Examiner* — Mohamed Charioui
*Assistant Examiner* — Elias Desta
(74) *Attorney, Agent, or Firm* — SNR Denton US LLP

(57) ABSTRACT

A defect repair apparatus includes a defect detection unit, a database, a defect repair unit, and a control unit. The defect detection unit inspects a multilayer substrate on which a repetitive pattern is formed and extracts positional information on a defect in the repetitive pattern and feature information on the defect. In the database, a plurality of defect repair techniques are registered. The defect repair unit repairs the defect of the multilayer substrate by a defect repair technique specified. The control unit reads a defect repair technique for the defect detected by the defect detection unit and controls the defect repair unit that repairs the defect by using the defect repair technique.

9 Claims, 32 Drawing Sheets

Basic structural example

Area information of template
Layer 1:Label 2
Layer 2:Label 2
Layer 3:Label 2
Layer 4:Label 2,Label 3,Label 6

Area information of template
Layer 1:Label 2
Layer 2:Label 2
Layer 3:Label 2
Layer 4:Label 2,Label 3
Layer 6:Label 2
Layer 7:Label 2

Registered layer group

Equipotential areas　　　Areas connected through contact hole

Registered layer group

Registered layer group

DEFECT REPAIR APPARATUS AND DEFECT REPAIR METHOD

BACKGROUND OF THE INVENTION

1. Field of the Invention

The present invention relates to a technique of defect repair that is performed in processes of manufacturing a display apparatus. In particular, the present invention relates to a defect repair apparatus and a defect repair method that are desirable for repairing a defect in a device pattern or a wiring pattern formed on a substrate such as a TFT (thin film transistor) substrate of a flat panel display (FPD).

2. Description of the Related Art

These days, as a display apparatus, a so-called flat panel display such as an organic EL (electro-luminescence) display and a liquid crystal display is popular. The display apparatuses are each formed of a wiring substrate including various conductive members such as elements including a thin film transistor (TFT) and a capacitor and a plurality of wirings (e.g., signal wiring and potential supply wiring) electrically connected to the elements.

In mass production of the wiring substrate that partly constitutes the display apparatus, a so-called defect such as a short circuit and disconnection may sometimes be generated by a foreign substance, for example. The short circuit means that a wiring and an element that are normally separate are electrically connected with each other. The disconnection means that a wiring and an element that are normally continuously provided are separated from each other. In the mass production, with increasing size of the display apparatus, the number of defects generated in a TFT substrate serving as a wiring substrate for driving the display apparatus is increased, which results in reduction in yield. To prevent this, defect repair processes for repairing defects are necessary.

As a technique of repairing the defect such as the short circuit and the disconnection, a technique of disconnecting a short-circuited portion through irradiation with laser light (laser repair), a technique of connecting a disconnected portion by a laser CVD (chemical vapor deposition) method, or the like is used.

For example, there has been proposed a defect repair method in which a defect repair technique is checked and selected based on CIM (computer integrated manufacturing) information on a substrate and defect coordinates, to thereby repair the defect automatically (see, for example, Japanese Patent Application Laid-open No. 2005-221974 (hereinafter, referred to as Patent Document 1)).

In addition, there has been proposed by the inventors of the present invention a defect repair method in which a unit pixel (wiring portion) on a substrate is sectioned into a plurality of areas and an appropriate repair technique is selected for each area, to thereby repair the defect (see, for example, Japanese Patent Application Laid-open No. 2008-159930 (hereinafter, referred to as Patent Document 2)).

SUMMARY OF THE INVENTION

However, as disclosed in Patent Document 1, in a case where the repair is simply performed on the assumption that a difference image between a defect image (suspected image) and a reference pattern image (reference image) is determined to be a defect range, if a position and a type of the defect and a condition of a defect portion on a substrate are not grasped, the repair may be failed. This is because a selection of a defect repair technique and a selection of various parameters such as a pulse period of laser light with which the defect is irradiated, a laser power, a spot shape of laser light, and an oscillation time period thereof depend on a skill and experience of an operator and selection results vary depending on them.

In a case of the TFT substrate or the like for display use, a wiring portion corresponding to each pixel has a plurality of potential supply wirings in addition to signal wirings and scanning wirings, and therefore a wiring density in each pixel is markedly increased and a pixel structure is significantly complicated.

For example, for repairing defects generated in contact with the same wiring or defects generated at almost the same position in the wiring portion, it is also necessary to select a defect repair technique depending on types of a member disposed therearound or presence/absence of a member. Further, in a case where a short-circuited portion is tried to be disconnected by, e.g., laser irradiation, it is necessary to prevent causing transformation of a thin-film transistor (TFT) therearound due to heat diffusion.

Specifically, there are a case where the types or positions of wirings that constitute a wiring portion (pixel) are complicated like an organic EL display and a case where a wiring portion is constituted of an one-end drive wiring and a both-end drive wiring, such as a potential supply wiring, both ends of which are connected to a power source. In those cases, the number of options of the defect repair techniques is excessively increased, which makes it difficult to select an appropriate repair technique.

As described above, in panel manufacturing processes of a flat panel display, defect generation patterns and the options of defect repair techniques (repair processes) for coping with the patterns are significantly diversified. When a plurality of portions have to be irradiated with laser light to repair one defect, it requires time and effort to set laser light irradiation conditions (laser process parameters), resulting in reduction in operation efficiency.

Thus, in defect repair processes on the panel manufacturing line, a skilled operator checks a defect and determines a defect repair technique on site, so excessive cycle time is required. As a result, there arises a problem in that an operation speed in the defect repair processes is difficult to catch up with a mass production speed of the entire line.

To avoid this problem, in a large number of panel manufacturing plants, a plurality of defect repair apparatuses (repair apparatuses) are equipped and the number of operators in charge of operating the defect repair apparatuses is increased.

However, this countermeasure for the above problem causes a serious problem of marked decrease in profits because the manufacturing cost and man-hour cost are increased by the significant increase in number of the defect repair apparatuses and the operators.

In view of the above-mentioned circumstances, it is desirable to significantly increase the operation efficiency in the defect repair processes and increase defect repair quality.

According to an embodiment of the present invention, a substrate on which a repetitive pattern is formed is inspected, and positional information on a defect in the repetitive pattern and feature information on the defect are extracted. Subsequently, a defect repair technique for the defect detected is read from a database based on a layer structure of the substrate. Then, a defect repair unit that repairs the defect by using the defect repair technique read is controlled.

Specifically, a control unit compares a constituent of area information (first area information) of an actual defect with a constituent of pre-registered area information (second area information) corresponding to the defect in the repetitive pattern, to read the defect repair technique from the database based on a result of the comparison.

According to another embodiment of the present invention, positional information of a defect in a repetitive pattern and feature information of the defect are detected from a substrate, and a defect repair method (template) corresponding to the defect detected is automatically read from a database based on a layer structure of the substrate. In addition, the defect is repaired based on the defect repair technique read. As a result, an appropriate defect repair method based on the layer structure of the substrate on which the repetitive pattern is formed is automatically selected and a defect repair is carried out by the defect repair technique selected.

As described above, according to the embodiments of the present invention, an appropriate defect repair method based on the layer structure of the substrate on which the repetitive pattern is formed is automatically selected. As a result, the operation efficiency in the defect repair processes is significantly increased. In addition, it is possible to reduce the manufacturing cost and man-hour cost because selection of an appropriate defect repair method based on the layer structure of the substrate and execution of the defect repair are automatically performed.

These and other objects, features and advantages of the present invention will become more apparent in light of the following detailed description of best mode embodiments thereof, as illustrated in the accompanying drawings.

DESCRIPTION OF PREFERRED EMBODIMENTS

Hereinafter, embodiments of the present invention will be described with reference to the attached drawings.

The description will be given on the following items in sequence.
1. First Embodiment
2. Modified Examples In this embodiment, a description will be given on a case where a target wiring substrate forms a display apparatus, that is, a case where a large number of wiring portions that constitute the wiring substrate formed of a TFT substrate and the like are formed in a two-dimensional matrix pattern so as to correspond to pixels of the display apparatus.

Figure 1:
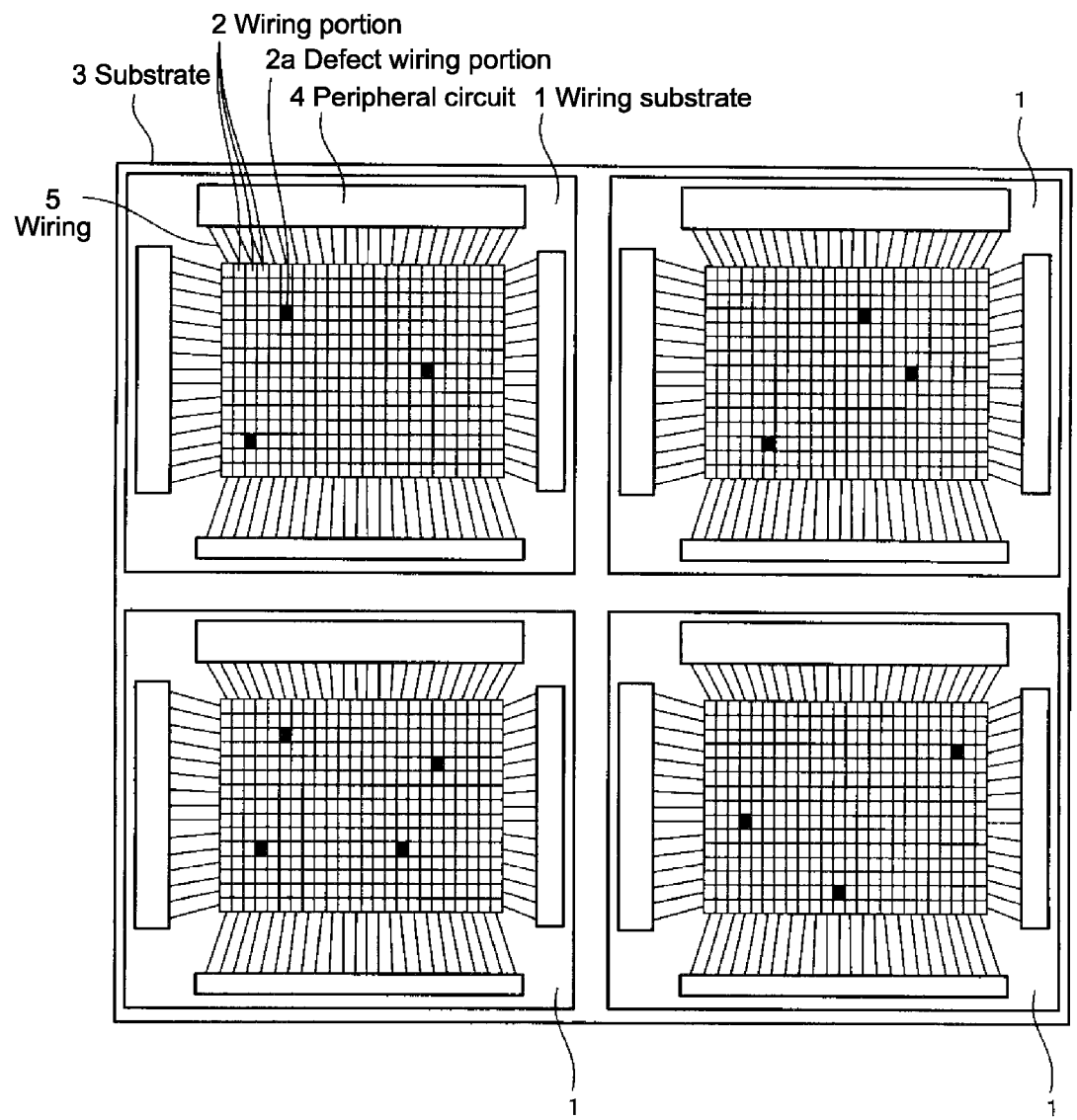
FIG. 1 is a diagram showing a structural example of a substrate as a check target.

FIG. 1 is a diagram showing an example of a substrate as a repair target in manufacturing processes of a flat panel display in this embodiment of the present invention.

Figure 2:
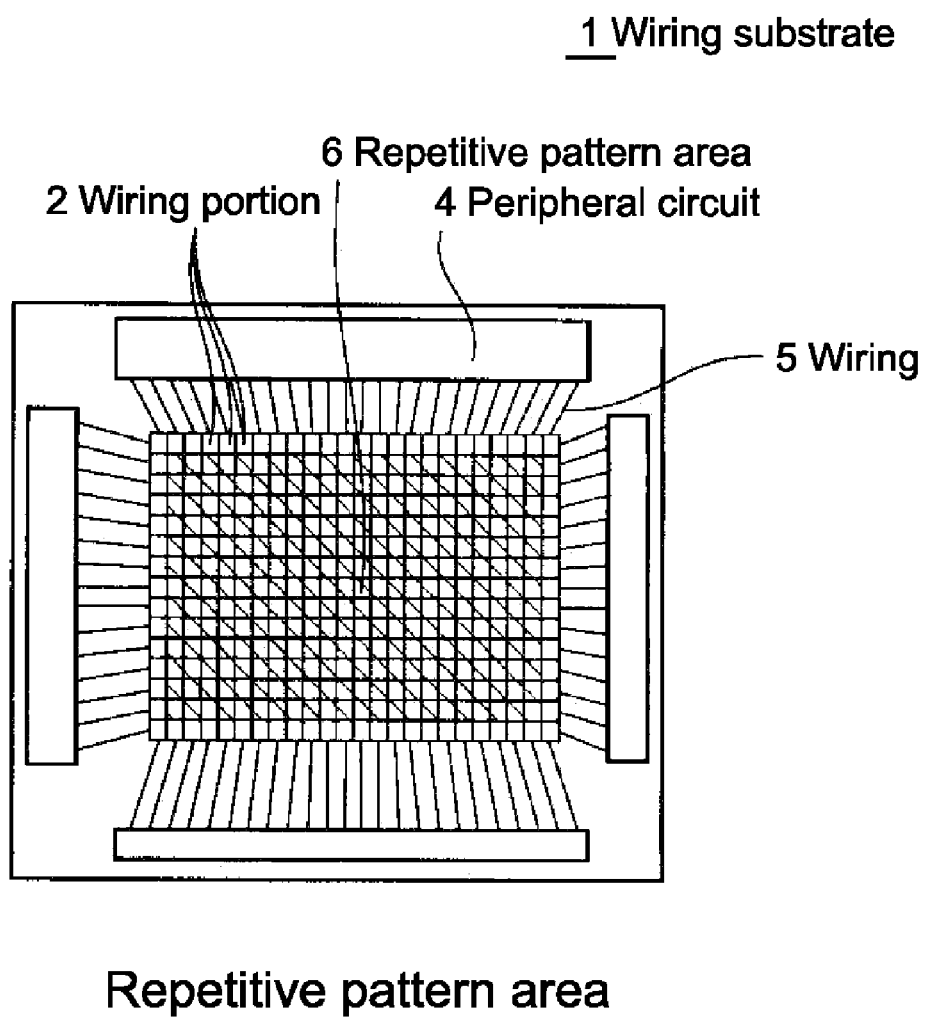
FIG. 2 is a diagram showing a repetitive pattern area in the substrate shown in FIG. 1.

In this example, wiring substrates 1 for four flat panel displays are formed on a substrate 3 at the same time. The wiring substrate 1 is divided into an area having a repetitive pattern (repetitive pattern area 6 (see FIG. 2)) (described later), an area having a peripheral circuit 4 that connects the repetitive pattern area 6 to outside through wirings 5 (peripheral circuit area), and an area disposed outermost on a boundary between the repetitive pattern area 6 and the peripheral circuit area (outermost area). The repetitive pattern area 6 and the outermost area are obtained by forming wiring portions 2 in the two-dimensional matrix pattern so as to correspond to the pixels of the flat panel display. As shown in FIG. 2, the repetitive pattern area 6 is a part excluding the outermost area from the area in which the wiring portions 2 are repetitively formed.

Figure 3:
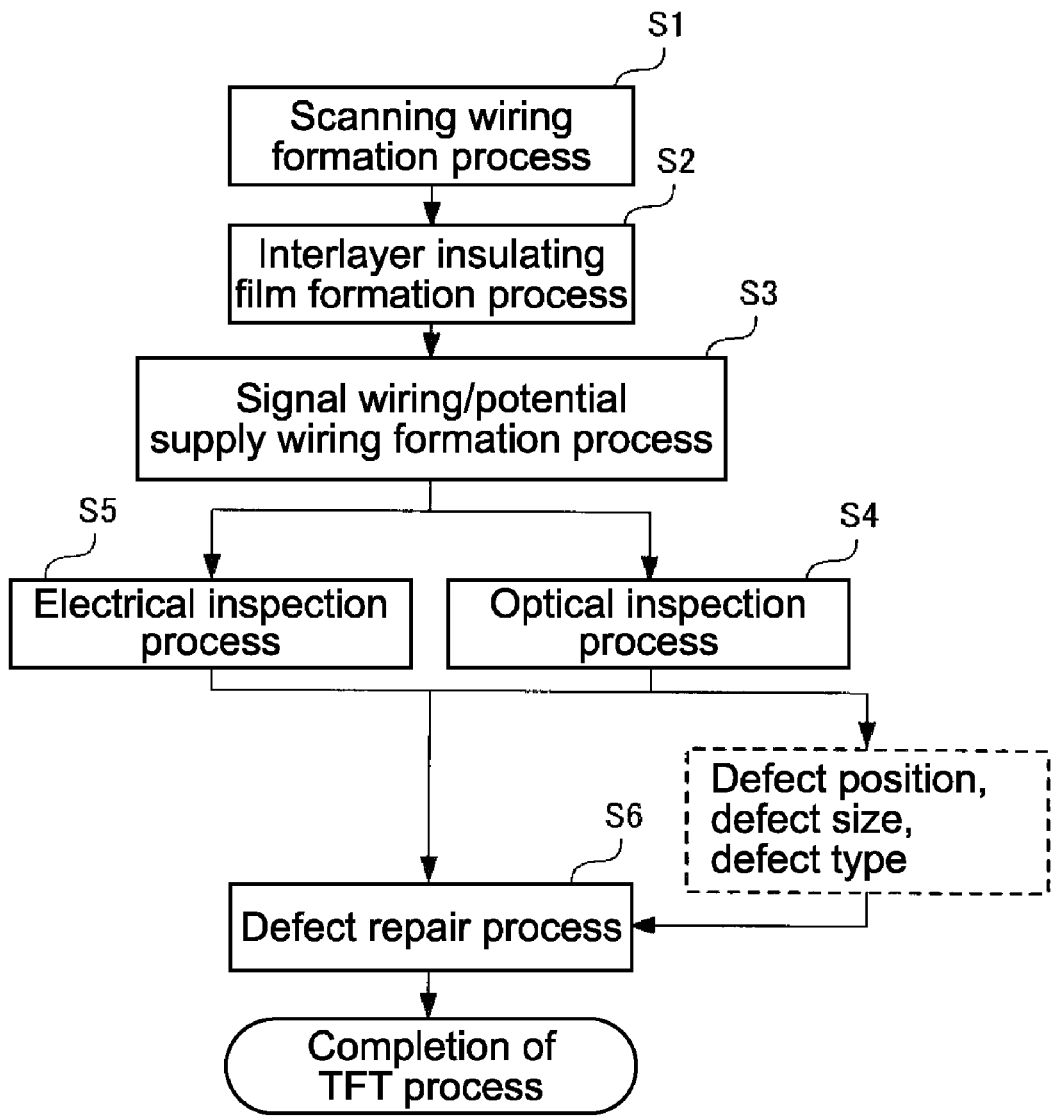
FIG. 3 is a flowchart showing a manufacture process of a wiring substrate of a flat panel display.

FIG. 3 is a flowchart showing the manufacturing process of the wiring substrate of the flat panel display, that is, a flow of a wiring pattern formation process, a defect inspection process, and a defect repair process in sequence.

In this embodiment, the wiring portion formation process is carried out by layering a scanning wiring, an interlayer insulating film, a signal wiring, and a potential supply wiring as a main structure of the target wiring portion 2 on the substrate 3 (Steps S1, S2, and S3). Further, the peripheral circuit 4 and the wiring 5 are formed, and the peripheral circuit 4 and the wiring portion 2 in the outermost area are connected. The formation process of the peripheral circuit 4 and the wiring 5 may be carried out before or after the formation process of the scanning wiring, the interlayer insulating film, the signal wiring, and the potential supply line in Steps S1 to S3.

Subsequently, an optical inspection process in which a defect wiring portion 2a is detected by optically observing the large number of wiring portions 2 is carried out with respect to the substrate 3 conveyed after being subjected to the wiring portion formation process (Step S4). When the defect wiring portion 2a is detected, positional information of the defect wiring portion 2a on the substrate 3 is sent to a computer (control unit) of a defect repair apparatus. In the optical inspection process, from an image including the defect wiring portion 2a (defect image) shown in FIG. 1, not only existence of the defect wiring portion 2a but also so-called pattern defect classification information including a defect (pattern defect, foreign substance, or the like) and a position thereof is specified. In addition, features of the defect, such as the size and the type (material, condition, or the like) thereof, are specified.

Further, a defect generated in an area other than the surface, which is hardly detected in the optical inspection process, is detected in an electrical inspection process (Step S5).

Further, in the defect repair process, by reading the defect positional information, a stage of the defect repair apparatus is controlled to move to the defect position. Then, the defect is checked by an observation system and repaired by performing laser irradiation or the like (Step S6). An appropriate repair method varies depending on the areas in which the defect is generated on the wiring substrate 1 on the substrate 3. When this process is ended, a TFT process (wiring substrate manufacturing process) is completed.

According to the present invention, the defect repair process can be significantly efficiently performed by calling repair data stored. Further, the defect repair process can be automatically performed by selecting repair data that is appropriate to the defect position.

Figure 4:
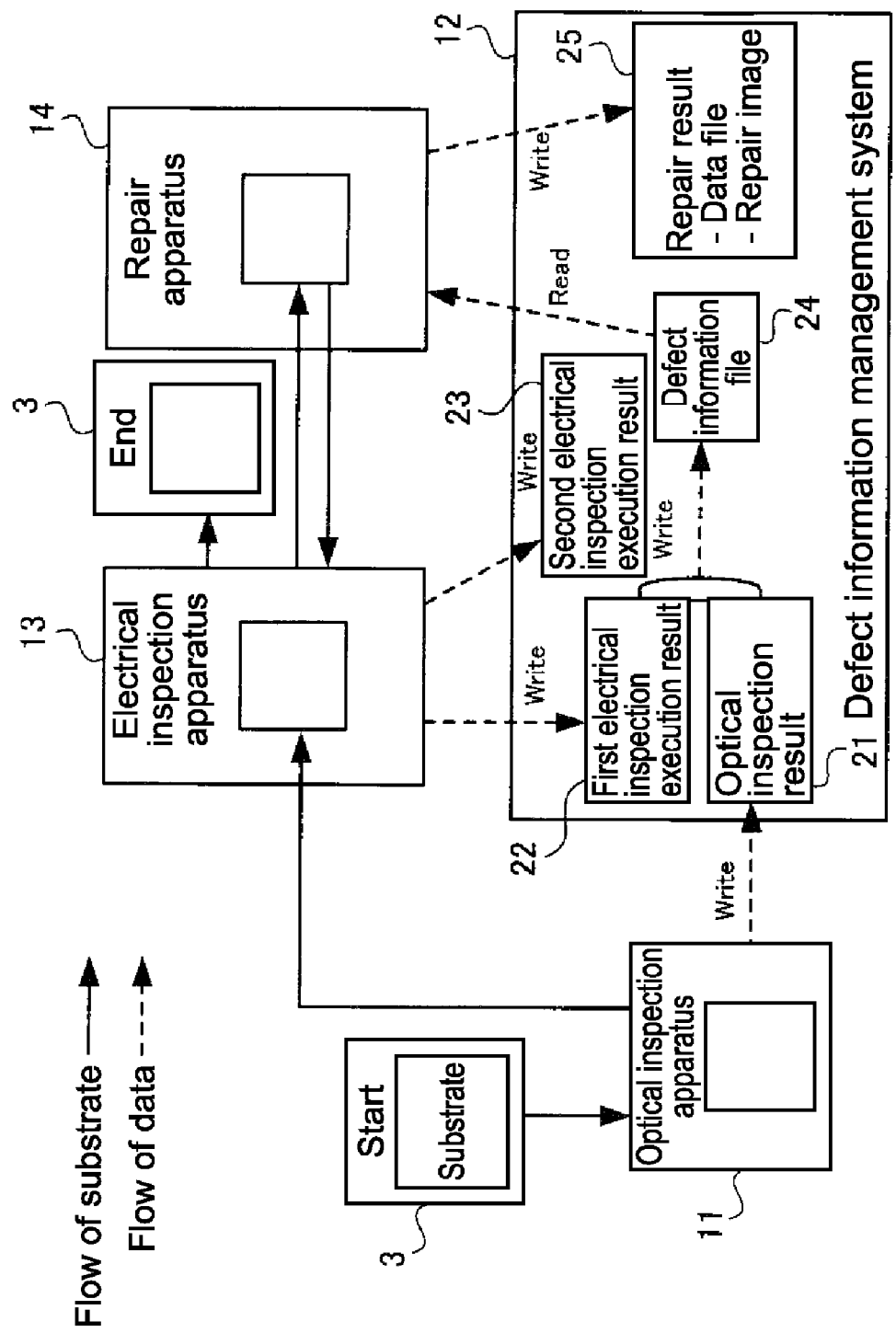
FIG. 4 is a diagram showing a specific flow from a defect check process to a defect repair process.

FIG. 4 is a diagram showing a specific flow from the defect inspection process to the defect repair process shown in FIG. 3.

The substrate 3 that has been subjected to the wiring portion formation process is moved to an optical inspection apparatus 11 (first step), the optical inspection is performed to identify a defect, and an inspection result 21 is output to a defect information management system 12 (second step). In addition, the substrate 3 is moved to an electrical inspection apparatus 13 (third step), the electrical inspection is performed to identify the defect, and an inspection result 22 is output to the defect information management system 12 (fourth step). The defect information management system 12 generates defect information obtained from one of the inspection results or obtained by associating the inspection results with each other (fifth step) and records the defect information on a memory as a defect information file 24. Meanwhile, the substrate 3 is moved from the electrical inspection apparatus 13 to a repair apparatus 14 (sixth step), and the repair apparatus 14 receives the defect information file 24 from the defect information management system 12.

The repair apparatus 14 automatically selects an appropriate repair technique (defect repair technique: template) based on a content of the defect information file 24 to carry out the repair, and outputs a repair result 25 (data file, image after repair, and the like) to the defect information management system 12 again (seventh step). In this case, the defect information file 24 received with the substrate 3 includes information on a layer structure of the substrate.

After that, when necessary, the substrate 3 is moved to the electrical inspection apparatus 13 (eighth step), the condition of the defect after the repair is checked again through the electrical inspection, and outputs the defect information to the defect information management system 12 again if necessary (ninth step). Further, the defect information is sent to the repair apparatus 14 via the defect information management system 12, the substrate 3 is moved to the repair apparatus 14 (tenth step), and the repair may be carried out again.

According to the embodiment of the present invention, a data file (template) of defect repair techniques (defect repair processes) that have been used and registered in advance can be called, with the result that the defect repair processes can be significantly efficiently performed. Further, the position, size, type, and the like of the defect are detected and appropriate repair data is selected, with the result that the defect repair processes can be automatically performed.

(Structural Example of Defect Repair Apparatus)

Figure 5:
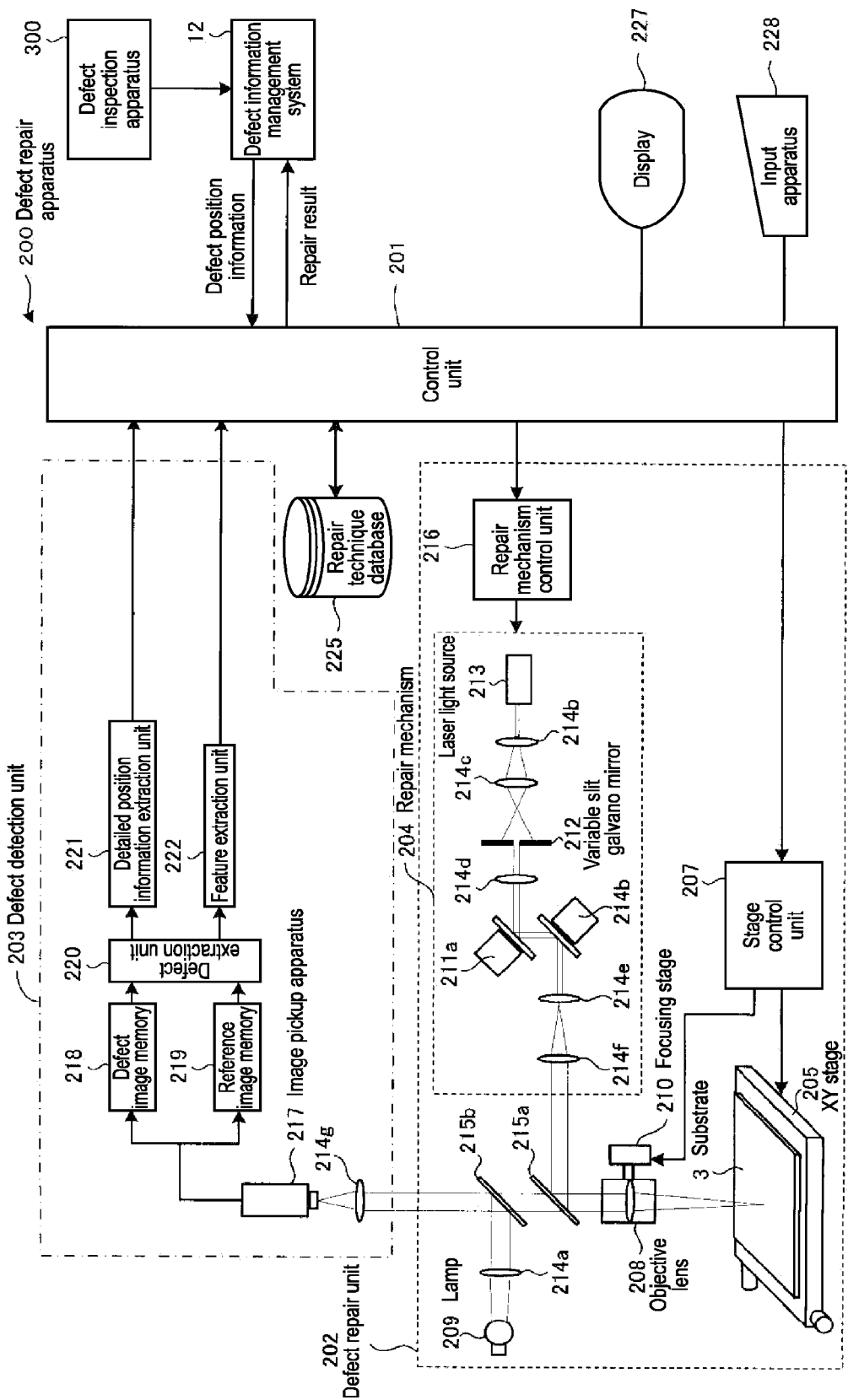
FIG. 5 is a diagram showing a structural example of a defect repair apparatus according to a first embodiment of the present invention.

FIG. 5 is a diagram showing a structural diagram of an example of a defect repair apparatus (corresponding to the repair apparatus 14) that carries out the defect repair processes with respect to the wiring substrate.

A defect repair apparatus 200 according to this embodiment is an example of a so-called laser repair apparatus that disconnects a short-circuited portion by performing laser light irradiation, but may be applied to an apparatus (see, for example, FIG. 5 of Patent Document 2) capable of performing a wiring connection process by a laser CVD method and the like. The defect repair apparatus 200 includes a processing apparatus capable of applying the laser CVD method between an objective lens 208 and the substrate 3, which is disclosed in detail in FIGS. 5 and 6 and the description thereof in the Patent Document 2.

The defect repair apparatus 200 is roughly constituted of a control unit 201, a defect repair unit 202, and a defect detection unit 203.

The control unit 201 is connected to a defect information management system 12 through a communication interface (not shown) or the like, and connected to a display 227 and an input apparatus 228 such as a keyboard.

The control unit 201 obtains in advance a result (defect information) of a defect inspection performed by a defect inspection apparatus 300 through the defect information management system 12 and controls, based on the defect information, the defect repair unit 202 that repairs the defect and the defect detection unit 203 that meticulously observes the defect. To the control unit 201, an MPU (micro processing unit) or a computer (processing unit) such as a personal computer can be applied.

In the control unit 201, a command is issued to a stage control unit 207 of the defect repair unit 202, an XY stage 205 on which the substrate 203 is mounted is moved, and adjustment is made so that a pixel in which a defect exists is positioned immediately below the objective lens 208. Then, a focusing stage 210 is moved to adjust an interval between the objective lens 208 and the substrate 3 so that a focusing point image of light passing through an optical lens 214g can be taken by an image pickup apparatus 217 of the defect detection unit 203. It should be noted that epi-illumination by using half mirrors 215a and 215b, an optical lens 214a, and a lamp 209 enables an image having appropriate brightness to be obtained. The image including the defect portion (defect image) taken is temporarily stored in a defect image memory 218. Here, the pixel corresponds to the defect wiring portion 2a shown in FIG. 1.

Next, the control unit 201 issues a command to the stage control unit 207 to move the XY stage 205 so that a position where a pixel pattern becomes completely the same as the pixel of the defect portion is located immediately below the objective lens 208. Then, an image having no defect (reference image) is taken and stored in a reference image memory 219. The pixel in this case corresponds to the wiring portion 2 shown in FIG. 1.

A defect extraction unit (defect detection unit) 220 performs position adjustment with respect to the defect image stored in the defect image memory 218 and the reference image stored in the reference image memory 219 and generates a difference image, thereby extracting an image of a defect portion. Then, the defect extraction unit 220 outputs the defect portion image extracted to a detailed positional information extraction unit 221 and a feature extraction unit 222.

The detailed positional information extraction unit 221 calculates an accurate portion of the extracted defect on the substrate 3 based on a current position of the XY stage 205 and the defect image, and sends the calculation result information to a repair method generation unit 226.

The feature extraction unit 222 quantifies various feature information items such as the color, size, contrast, and shape of the defect, which are used for specifying the pattern, type, and the like of the defect extracted by the defect extraction unit 220, and outputs the information items quantified to the control unit 201.

Subsequently, the control unit 201 reads, from a repair technique database 225, defect repair information (repair recipe information) (described later in detail) based on the detailed positional information and the feature information that are obtained by the detailed positional information extraction unit 221 and the feature extraction unit 222, respectively. By the defect repair information, operations of respective units in a repair mechanism 204 of the defect repair unit 202 are defined.

Specifically, for example, based on the detailed positional information from the detailed positional information extraction unit 221, the control unit 201 determines the position and condition of the defect portion on the wiring substrate and layer information thereof and performs control so that an appropriate defect repair process is carried out depending on the defect position.

In addition, as will be described later in detail, the control unit 201 displays, on the display 227, the repair technique (template) based on the defect repair information generated with the template being overlapped with the defect image. It should be noted that the control unit 201 can repair a part of a repair object of the defect repair information based on the defect information such as the position and the feature of the defect depending on a situation. Further, one defect repair information item may include a plurality of repair technique in some cases.

When the operator judges that the repair technique displayed on the display 227 is not appropriate, the operator can select another repair technique by operating the input apparatus 228 (input unit) such as the keyboard and a mouse or can change a part or whole of the repair technique (defect repair information). Further, when a plurality of defect repair techniques are read from the repair technique database 225 by the repair method generation unit 226, the plurality of defect repair techniques are displayed on the display 227 and the operator is urged to select one of the plurality of defect repair techniques. Subsequently, the defect repair is performed by the defect repair technique selected by operating the input apparatus 228 by the operator.

Upon reception of an operation signal input from the input apparatus 228, the control unit 201 records a selection history or a change history of the defect repair technique on the repair technique database 225. The repair techniques stored in the repair technique database 225 are used for future defect repair.

When the defect repair technique is determined, the control unit 201 issues a command to a repair mechanism control unit 216 according to the defect repair technique determined and causes the units in the repair mechanism 204 to operate, thereby repairing the defect. In the repair mechanism 204, a laser beam emitted from a laser light source 213 is corrected by optical lenses 214b and 214c and thereafter caused to pass through a variable slit 212, thereby making it possible to change an irradiation size and an irradiation angle.

The variable slit 212 is referred to as an XY-θ slit, for example, and has rectangular opening lengths in X and Y directions and can be rotated by a θ-degree angle and driven based on a drive signal from the repair mechanism control unit 216.

The laser beam that is shaped by the variable slit 212 passes through an optical lens 214d and is reflected by galvano mirrors 211a and 211b. The galvano mirrors 211a and 211b are mirrors whose angles can be varied two-dimensionally. By driving the galvano mirrors 211a and 211b based on the control by the repair mechanism control unit 216, it is possible to adjust an optical axis of the laser beam, i.e., an irradiation position thereof within a visual field of the objective lens 208 without moving the XY stage 205.

The defect repair apparatus 200 including the variable slit 212 and the galvano mirrors 211a and 211b can irradiate the defect with the laser beam with sufficient positional accuracy, and therefore can repair the pattern defect with accuracy.

Further, the laser beam reflected by the galvano mirrors 211a and 211b passes through optical lenses 214e and 214f and is reflected by the half mirror 215a, and then the substrate 3 is irradiated with the laser beam through the objective lens 208, thereby repairing the defect.

The defect inspection apparatus 300 can use the optical inspection apparatus for searching the defect, and therefore it is possible to repair a pattern defect whose conduction state is normal.

The control unit 201 will be described in more detail.

Figure 6:
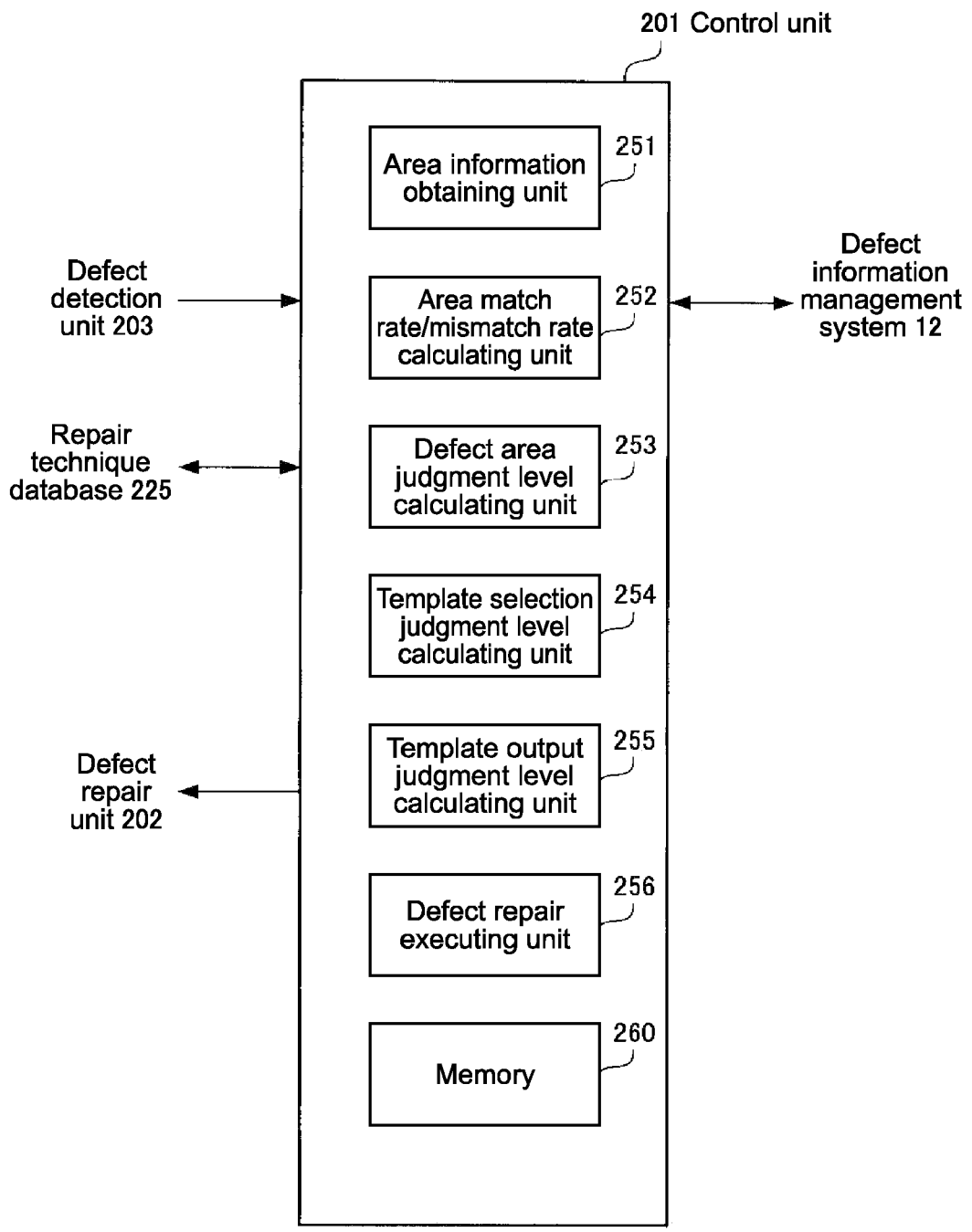
FIG. 6 is a diagram showing an inner structure of a control unit shown in FIG. 5.

FIG. 6 is a block diagram showing an inner structure of the control unit 201. The control unit 201 includes an area information obtaining unit 251, an area match rate/mismatch rate calculating unit 252, a defect area judgment level calculating unit 253, a template selection judgment level calculating unit 254, a template output judgment level calculating unit 255, a defect repair executing unit 256, and a recording unit 260. For the recording unit 260, a non-volatile memory such as a semiconductor memory is used. The respective processing units will be described later.

(Defect Repair Process)

Figure 7:
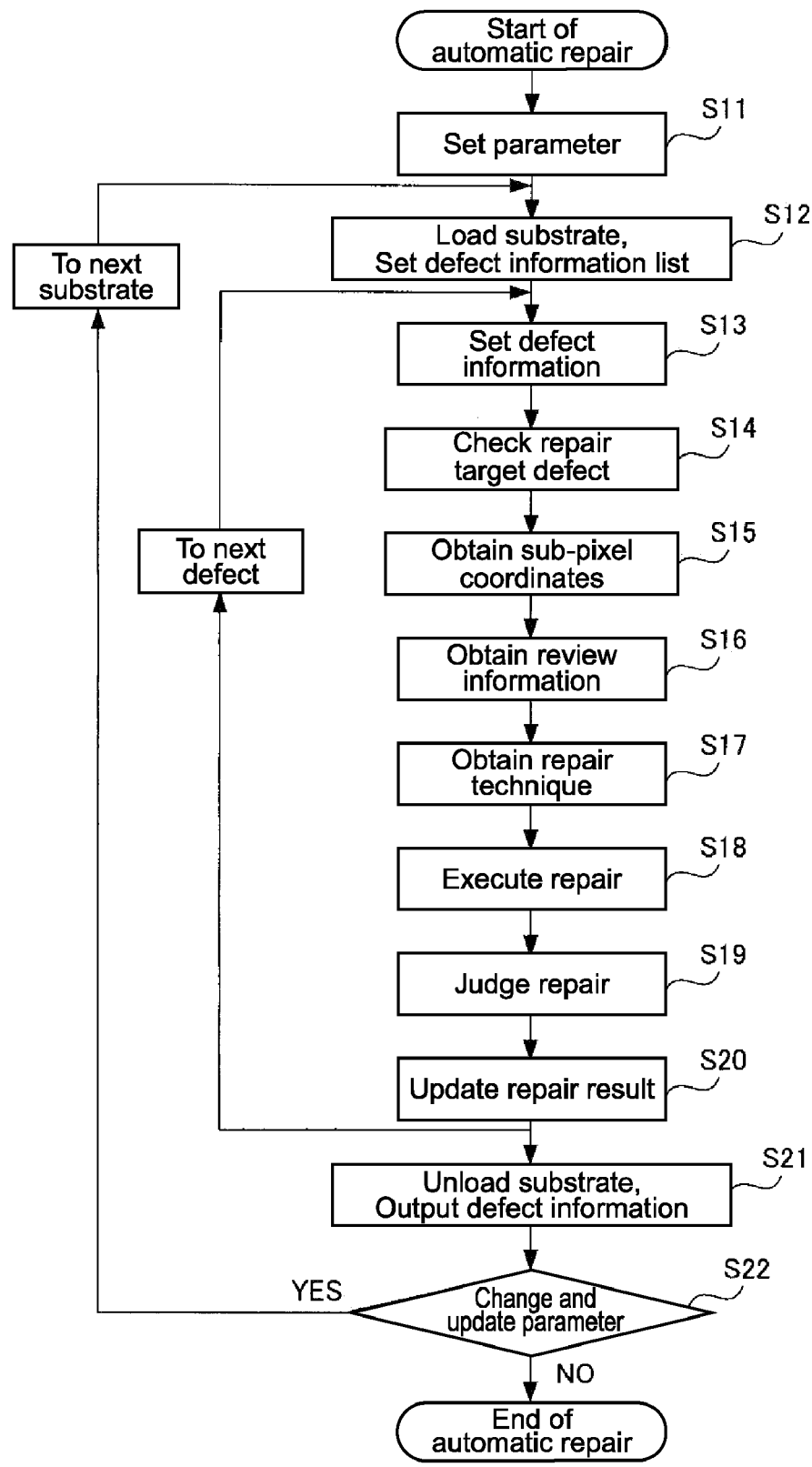
FIG. 7 is a flowchart showing a defect repair process according to the first embodiment of the present invention.
Figure 8:
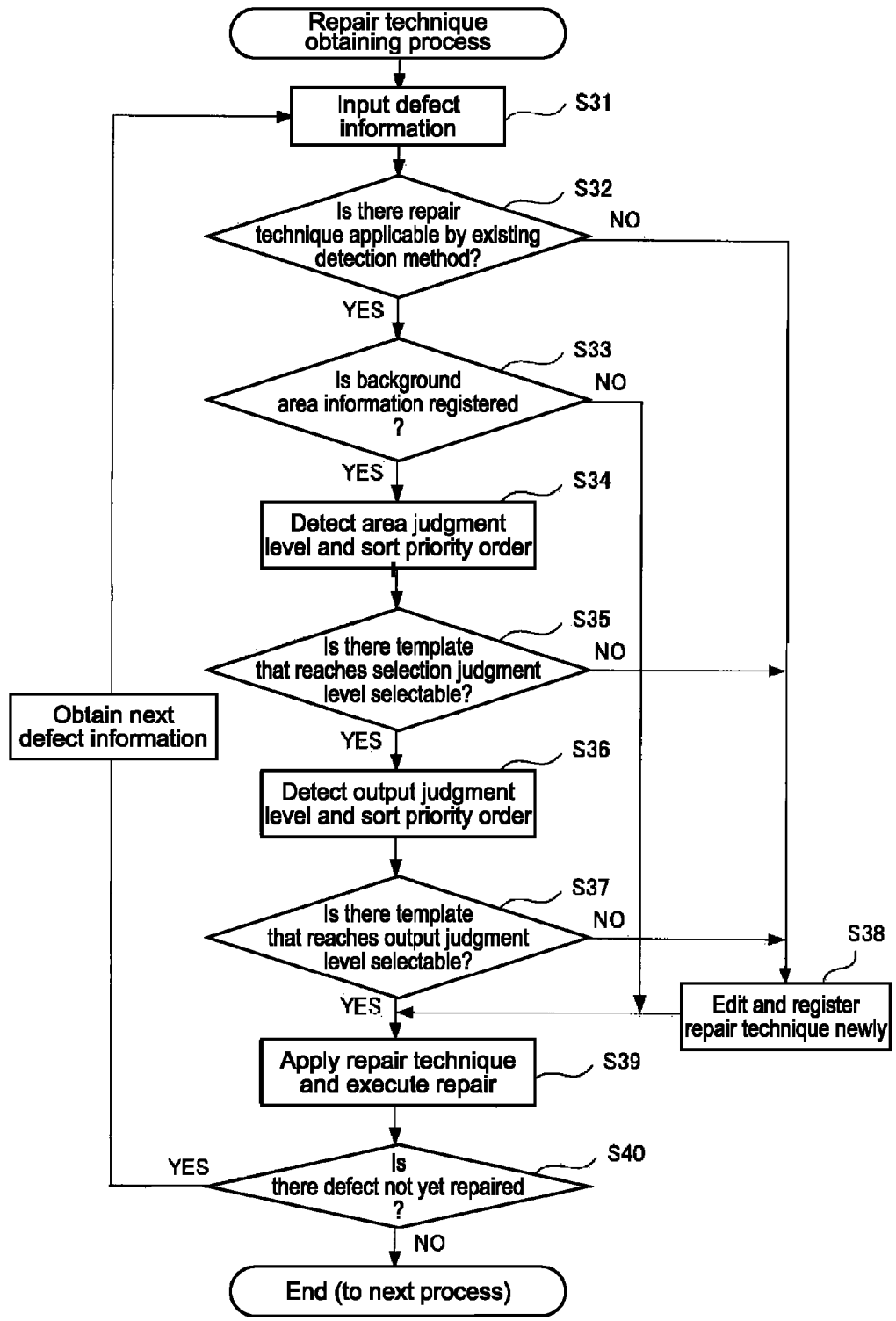
FIG. 8 is a flowchart showing a defect repair technique obtaining process according to the first embodiment of the present invention.

With reference to flowcharts shown in FIGS. 7 and 8, a description will be given on the defect repair process performed by the defect repair apparatus 200 along with a series of operations of the defect repair system constituted of the above-described structures. FIG. 7 is a flowchart showing a main routine of the series of defect repair process, and FIG. 8 is a flowchart relating to a repair technique obtaining process (Step S17) in the defect repair process.

Step S11: Setting of Parameters

The parameters are set for the defect repair apparatus 200. That is, the above-described basic information items used for performing the repair are set for the defect repair apparatus 200.

Specifically, the parameters refer to the basic information items relating to the substrate 3, such as the positions and the number of patterns, alignment mark positions, and the positions and the number of wiring portions 2 within the substrate 3 as repair targets. In addition, the basic information also includes the size and the condition of the defect as a target to be subjected to automatic repair, the frequency of the repair performed in the substrate 3, setting information of repair conditions such as a feature of a defect that should be repaired preferentially, the shape of a wiring pattern, databases of the repair techniques (which is applied when a plurality of databases are used), and the like. In the defect repair apparatus 200, those parameters are uniquely set.

Step S12: Conveyance of Substrate 3 and Setting of Input Information

The substrate 3 is conveyed from outside into the defect repair apparatus 200, and defect information of a previous process of the substrate 3 is input. The information on the substrate 3 conveyed and the defect information are checked with the parameters set in the defect repair apparatus 200, and the basic information of the substrate 3 as the repair target is determined, thereby performing an initial setting of the repair conditions (e.g., to clear repair process counts).

The defect information is the number of defects that are detected by the optical inspection and the coordinates thereof or pixel information (including information as to whether the defect is a line defect or a point defect) in the defect inspection apparatus 300. Alternatively, the defect information is obtained by associating a defect detected by the electrical inspection and a defect detected by the optical inspection with each other.

Step S13: Setting of Defect Information

From the list of the defect information items for each substrate 3, one defect information item is selected and input by one of methods of performing repair in the listed order, collectively repairing or sorting specific defects (for example, preferentially repairing linear defects), or selecting any one of defects by an operator of the defect repair apparatus 200.

Step S14: Checking of Defect Information

It is checked whether the repair can be automatically performed based on the defect information list of the substrate 3 which is input. Specifically, there may be a case where the defect information input is insufficient to perform the automatic defect repair, and it is checked whether this case occurs.

For example, the automatic defect repair may be difficult to be performed in a case where the repair condition of the current substrate 3 is not met, specifically, for example, in a case where a point defect extinction process is not performed the specific number of times, a case where the repair processes are not performed the specific number of times, or a case where there is a defect that has been subjected to the repair process. Further, for example, in a case where defect coordinates input is not defined or a case where it is clearly defined that the repair is not performed in the outside of a pattern, the automatic defect repair may not be performed. The details of those conditions are disclosed in FIG. 4, etc., of Japanese Patent Application Laid-open No. 2008-155263 by the applicant of the present invention.

Step 15: Obtainment of Defect Positional Information

When it is judged that the defect information input is a defect to be repaired, detailed coordinate information of the defect is obtained. Specifically, from defect coordinates obtained by the optical inspection result, a pixel number obtained by the electrical inspection result, or the like, a position at which the defect is actually generated is calculated. It should be noted that the content of Step S15 is expressed as "obtain sub-pixel coordinates" in FIG. 17.

Step S16: Taking of Defect Image

When the detailed position of the defect is obtained, the XY stage 205 is moved, the defect image is taken, and detailed defect information in the pattern is obtained. It should be noted that the content of Step S16 is expressed as "obtain review information" in FIG. 7.

Step S17: Defect Repair Technique Obtaining Process

This step is a characteristic step of the present invention. By checking the detailed defect information obtained from the defect image with the defect repair techniques, an optimal defect repair technique is retrieved from the repair technique database 225 and is output with the positional information of the defect. It should be noted that the content of Step S17 is expressed as "obtain repair technique" in FIG. 7. The process of this step will be described in detail with reference to FIG. 8.

Step S18: Repair Execution Process

The defect repair process is set in accordance with an actual position of the defect, a positional correction is performed if necessary, and thereafter the defect is repaired. A repair execution result in this case is stored additionally in the recording unit 260 or the repair technique database 225, for example. It should be noted that the content of Step S18 is expressed as "execute repair" in FIG. 7.

Step S19: Repair Judgment Process

When the execution of the repair is completed, an image after the repair is taken at the same coordinates and factor of the position at which the defect image is picked up. Those images are compared with each other, thereby performing simple judgment as to whether the repair has been appropriately performed.

Step S20: Repair Result Update Process

The result of the repair is updated. The content of the update includes judgment as to whether the repair has been appropriately performed, the detailed content of the repair, the number of repair processes performed, the number of point defect extinction processes performed, and the like. After the repair result is updated, the list of the defect information is checked again, and it is judged whether a defect unprocessed remains or not or whether the repair is completed. Based on the judgment, it is determined whether the repair process is continues by additionally inputting another defect information item or the repair is terminated and the substrate 3 is conveyed to outside.

In this case, when it is determined that the defect unprocessed still remains, the process returns to Step S12.

Step S21: Conveying of Substrate, Setting of Repair Information

In a case where all the defects are repaired with respect to the substrates 3 input, or in a case where a repair termination condition is met, the substrate 3 is conveyed and the detect repair information is output to the defect information management system 12. The repair termination condition refers to a condition that the repair is performed the specified number of times or more, a condition that the point defect extinction process is performed the specified number of times or more, a condition that the repair is performed on a specific defect, or the like.

Step S22: Update of Parameter

In a case where the defect repair technique is newly registered in the above-described processes, or in a case where the power of the laser or the condition of a defect to be repaired should be changed, the parameter information stored in the repair technique database 225 of the defect repair apparatus 200 is updated and the next substrate 3 is set.

FIG. 8 is a flowchart showing the defect repair technique obtaining process (Step S17) by the control unit 201. The flowchart of FIG. 8 relates to the repair technique obtaining process (in particular, prioritizing process) of the defect repair process.

First, in Step S31, the defect information is input from the detailed positional information extraction unit 221 and the feature extraction unit 222 to the control unit 201, and the process proceeds to Step S32.

Next, in Step S32, it is judged whether there is a defect repair technique (template) applicable by an existing detection method, and the process proceeds to a subsequent step depending on the judgment result. There have been proposed a plurality of existing detection methods such as a method of reading a higher-priority defect repair technique based on the positional information, area information, and the feature information of the defect (see, Japanese Patent Application Laid-open No. 2007-163892). In addition, there has also been proposed a method of reading a defect repair technique by dividing the wiring substrate into a plurality of areas and being based on areas including defects on the wiring substrate (see, Japanese Patent Application Laid-open No. 2008-155263). Furthermore, there has also been proposed a method of automatically reading a defect repair technique based on a positional relationship between reference coordinates of the wiring pattern and the defect detected (see, Patent Document 2). In a case where there is the defect repair technique, the process proceeds to Step S33. In a case where there is no defect repair technique, the process proceeds to Step S38.

In Step S33, it is judged whether defect background area information is registered. If the area information is registered, the process proceeds to Step S34. If the area information is not registered, the process proceeds to Step S39.

In Step S34, a defect area judgment level is detected, and a priority order is sorted (classified or rearranged), and then the process proceeds to Step S35. Specifically, the area match rate/mismatch rate calculating unit 252 calculates the match rate and the mismatch rate between the defect and the template, and based on a calculation result obtained, the defect area judgment level calculating unit 253 calculates the defect area judgment level.

In Step S35, the template selection judgment level calculating unit 254 judges whether an applicable template selection judgment level is reached. If a predetermined template selection judgment level is reached, the process proceeds to Step S36. If the predetermined template selection judgment level is not reached, the process proceeds to Step S38.

In Step S36, the template output judgment level calculating unit 255 detects a template output judgment level and sorts a priority order. Then, the process proceeds to Step S37.

In Step S37, the template output judgment level calculating unit 255 judges whether an applicable template output judgment level is reached. If a predetermined template output judgment level is reached, the process proceeds to Step S39. If the predetermined template output judgment level is not reached, the process proceeds to Step S38.

In Step S38, in accordance with an operator's instruction from the input apparatus 228, a new defect repair technique is edited and registered, and the process proceeds to Step S39.

In Step S39, the defect repair executing unit 256 applies the defect repair technique that meets the condition in Step S37 or the defect repair technique edited and registered in Step S39 and sends a control signal to the defect repair unit 202, thereby controlling execution of the defect repair. Upon completion of the process, the process proceeds to Step S40.

In Step S40, it is judged whether there is a wiring portion having a defect that is not yet repaired. At this time, if it is judged that there is the wiring portion having the defect that is not repaired, the process returns to Step S31, and new defect information is input. On the other hand, if it is judged that there is no wiring portion having the defect that is not repaired, the series of processes are terminated, and the process proceeds to subsequent steps.

Figure 9:
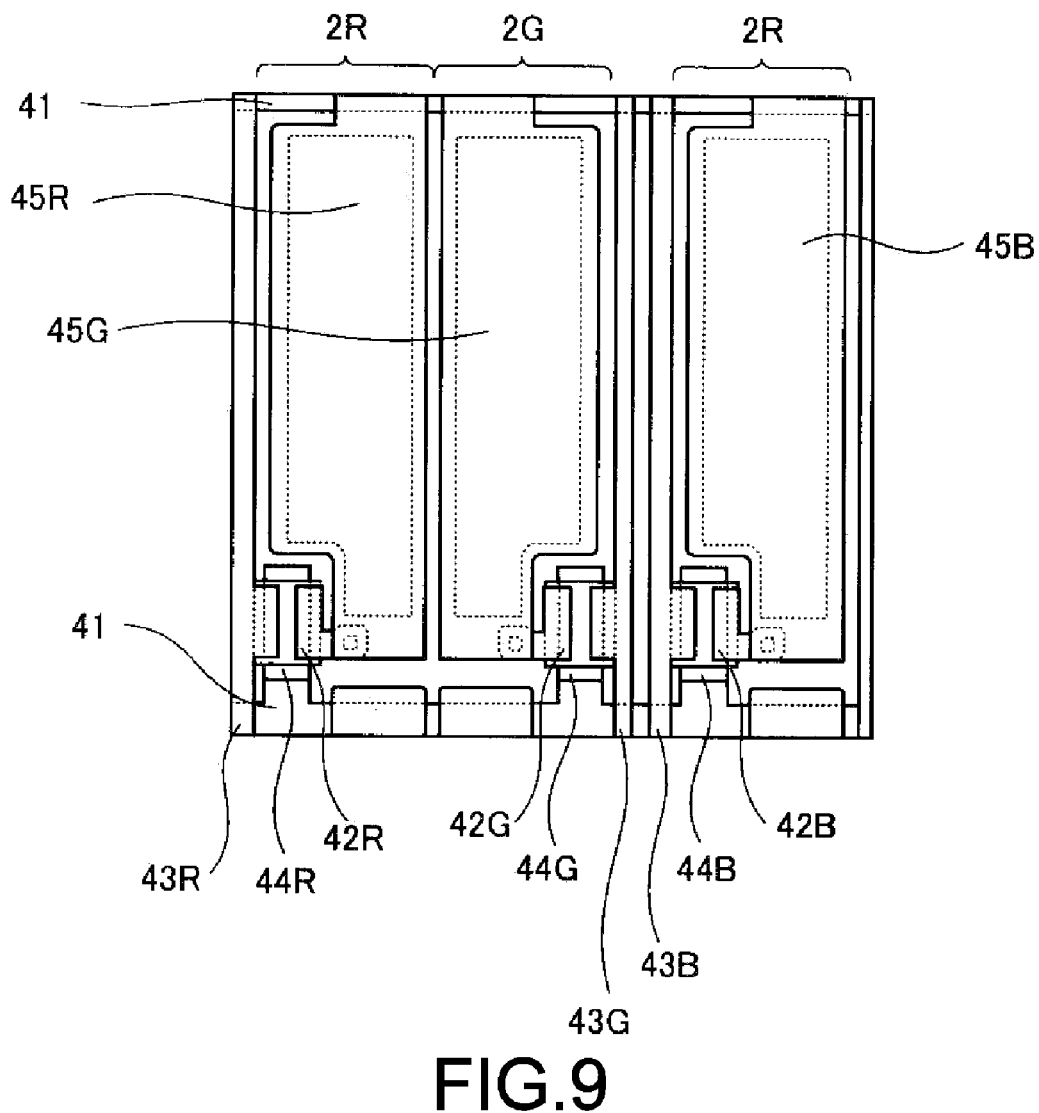
FIG. 9 is a diagram showing a wiring pattern (wiring portion)

Here, FIG. 9 is a diagram showing a schematic structure of the wiring portion 2 (unit pixel) formed in the repetitive pattern area 6 of the wiring substrate 1.

The wiring portion 2 is divided into three areas (hereinafter, also referred to as "sub-area") 2R, 2G, and 2B corresponding to three primary colors RGB, for example. The three sub-areas 2R, 2G, and 2B have different structures in that the three sub-areas 2R, 2G, and 2B include different capacitors (capacitative elements) 45R, 45G, and 45B. In this embodiment, the three sub-areas 2R, 2G, and 2B having partly different shapes (structures) are used as an example, but the three sub-areas may of course have the same shape (structure).

The sub-areas 2R, 2G, and 2B are formed to have approximately the same area, and have structures in which signal wirings 42R, 42G, and 42B, potential supply wirings 43R, 43G, and 43B, a ground electrode (not shown) are arranged on scanning lines 41 provided on the wiring substrate 1 (see, FIG. 1) via an interlayer insulating film (not shown) extendedly in a direction perpendicular to the scanning lines 41, respectively. The signal wirings 42R, 42G, and 42B have structures of being opposed to the capacitors 45R, 45G, and 45B connected to the ground electrode (not shown) through gates of TFT elements 44R, 44G, and 44B, respectively.

It should be noted that FIG. 8 only shows the schematic diagram of the actual wiring pattern of the wiring portion 2 and therefore includes different points from the actual wiring pattern.

In the wiring pattern (wiring portion 2) having the repetitive pattern as shown in FIG. 9, in a case where a plurality of repair patterns can be provided depending on defect positions in a pixel, the repair technique to be applied may differ depending on the conditions. In this case, information as to which defect repair technique is used for which defect is registered in the repair technique database 225 in advance as a template. The template refers to an objectified (visualized) matter of the defect repair information (repair recipe information), that is, the defect repair technique.

Subsequently, effective is a technique in which the reference coordinates of the repetitive pattern (wiring portion 2) and the defect position are input, an optimal defect repair technique is retrieved from the repair technique database 225, the template is superposed on the defect image, and the defect repair technique is applied.

As the defect repair method using the template, a technique disclosed in Japanese Patent Application Laid-open No. 2007-163892 can be used.

Figure 10:
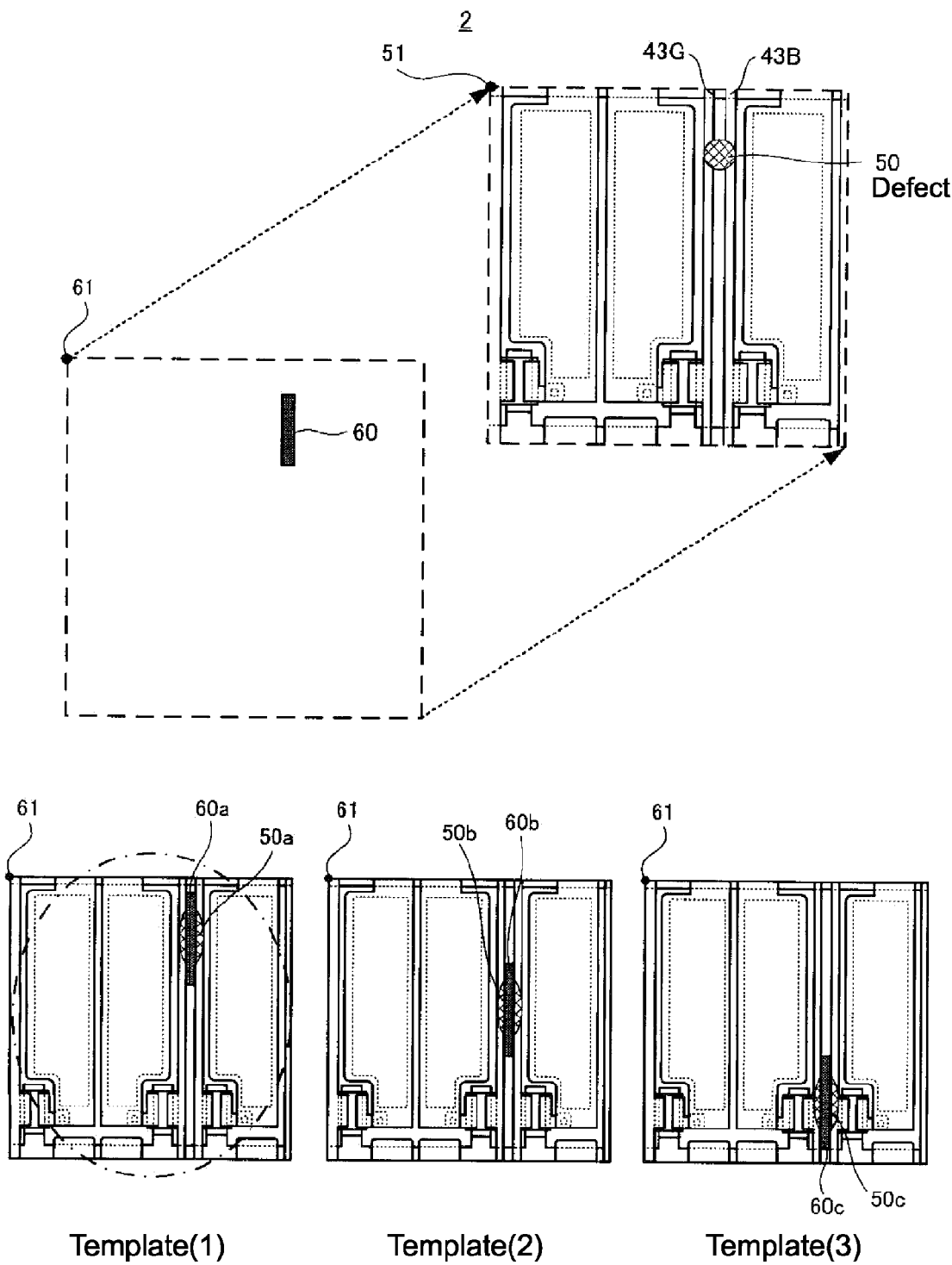
FIG. 10 is a diagram showing an example of a defect image and examples of templates.

FIG. 10 is a diagram showing an example of the defect image in which a short-circuited defect exists in a wiring part.

A defect 50 in the defect image is an example of the short-circuited defect in the wiring part (potential supply wirings 42G and 42B). First, in the detailed positional information extraction unit 221, reference coordinates 51 set at any corner of the wiring portion 2 and a repetitive pattern area 52 are detected. Then, based on a relative position from the reference coordinates 51, the position and condition of the defect 50 on the repetitive pattern are narrowed down. Subsequently, the control unit 201 selects a registered template that meets the condition of the defect 50 from the repair technique database 225.

The template includes a "defect object" that is a replica of the defect and a "repair object" that indicates a part to be subjected to the repair process depending on the position of the defect object on the wiring portion and a feature thereof. The defect object indicates, for example, the position of the defect object, an area to which the defect object belongs, the size and shape thereof, and a circuit where the defect object is located. In addition, the repair object indicates the position, output, and the like of laser light with which the defect is irradiated.

In this example, as the defect repair technique with respect to the defect 50 that causes the short circuit between the wirings, that is, defect objects 50a, 50b, and 50c, optimal templates (1) to (3) therefor are registered in the repair technique database 225.

In other words, in this example, as the defect repair technique depending on the position of the defect 50, the templates (1) to (3) are registered in the repair technique database 225, and an optimal template for the repair of the defect 50 is selected from the templates (1) to (3).

The template (1) includes a repair object 60a with respect to the defect object 50a having almost the same conditions such as the position and the size as the defect 50. In addition, the template (2) includes a repair object 60b with respect to the defect object 50b that is located slightly below the defect 50. Further, the template (3) includes a repair object 60c with respect to the defect object 50c that is located far below the defect 50.

In this example, the template (1) including the defect object 50a having almost the same conditions such as the position and the size as the defect 50 is selected as the optimal template for the repair of the defect 50.

Then, the template (1) read to the control unit 201 is displayed on the display 227. At this time, reference coordinates 61 of the template (1) are transformed with the reference coordinates 51 of the defect image (wiring pattern) being an origin, and the repair object 60a is superposed on the defect 50 of the defect image. The coordinate transformation method is disclosed in Patent Document 2 in more detail.

By the defect repair method in the repetitive pattern area as described above, the optimal template can be selected based on the position of the defect in the repetitive pattern (wiring portion). As a result, the defect repair process can be automated by reading the defect repair technique selected depending on the positional relationship, and thus a troublesome task of manually performing determination can be avoided.

It should be noted that in the case where there is no appropriate defect repair technique (template) for the defect as the repair target when the repair process is read from the repair technique database 225, a second best template is selected based on a predetermined priority order and the like. A template of a highest-priority (e.g., most-frequently-used) defect repair technique or a template of a low-difficulty-level defect repair technique is automatically selected, for example, and the selected template is displayed on the display 227.

Then, the repair technique by the template displayed is automatically carried out or visually confirmed by the operator and then carried out.

In addition, in a case where there is no appropriate process setting file (template) with respect to the defect as the target, the operator can operate the input apparatus 228 to manually set a laser process condition, and can add a setting file thereof to the repair technique database 225.

(Header Information and Object Information)

The defect repair technique displayed as the template in this embodiment is a data file including header information and object information associated with the header information (see, Japanese Patent Application Laid-open No. 2007-163892).

It should be noted that the defect repair technique is also referred to as "defect repair information (repair recipe information)".

The header information includes a "recipe name (or recipe number)" of the defect repair technique, an "area number" that indicates a sub-area in which the defect exists, a "sub-area number" that indicates the sub-area, a "reference pixel number" that indicates a position of a reference pixel on the substrate 3, an "adjacent pixel number" that indicates existence/nonexistence of an adjacent pixel on the sides, top, and bottom of the reference pixel and a position thereof, and an "object count" of the repair object that indicates the defect whose repair recipe is registered and the defect repair technique.

The object information includes the defect object that is the replica of the defect and the repair object that indicates a part to be subjected to the repair process depending on the position of the defect object in the wiring portion 2 and the feature thereof.

In other words, the object information is obtained by associating the defect object and the repair object with each other and registering them by the number of objects registered in the header information. It should be noted that the simple use of the term "register" means registration into the repair technique database 225 described above.

The object information includes a "recipe name (or recipe number)" for checking with a recipe header, "coordinates" that indicate a position of the object in the wiring portion 2, an "object shape", an "angle", and "position correction information" as basic information of the defect object and the repair object.

It should be noted that the "correction information" is information for performing position correction by comparison with the defect position of the actual defect image, and the "angle" is a rotation angle of the defect on the XY stage 205 from a regular position.

In this embodiment, applicable templates are narrowed down based on the area information of the area in which the defect exists in the repetitive pattern (wiring portion 2) and optimized. Hereinafter, the area in which the defect exists (or the area that is occupied by the defect) in the repetitive pattern is referred to as a "defect area" or "defect range" in particular.

(Regarding Area Information)

Next, a description will be given on a process by the area information obtaining unit 251.

Figure 11:
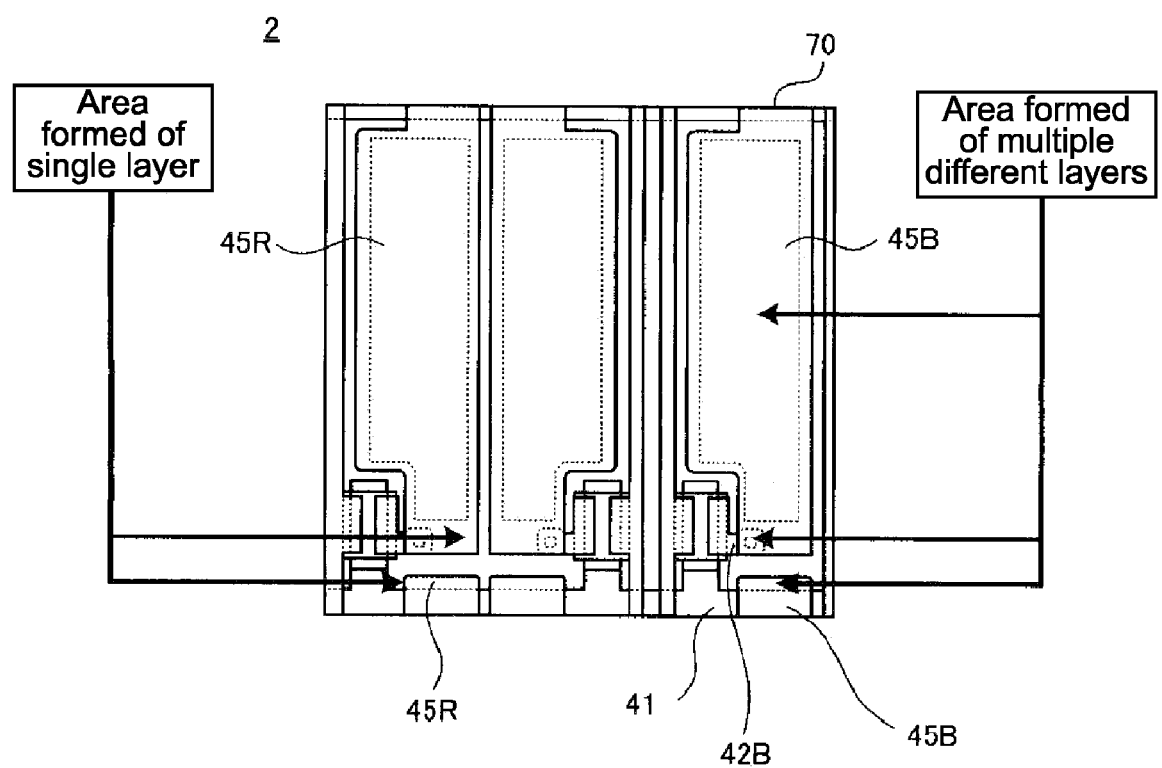
FIG. 11 is a schematic diagram showing a layer structure of the wiring pattern shown in FIG. 9.

FIG. 11 is a diagram schematically showing a layer structure of the repetitive pattern (wiring portion 2) shown in FIG. 9.

Because of a multilayer structure, below a specific layer, another layer is disposed in some cases. Therefore, there may be an area in which it may be difficult to recognize a structure of the specific layer only from an image 70 of the repetitive pattern. For example, when an area formed of a single layer, an area constituted of a plurality of different layers, and the like exist together, the layer structure is difficult to be recognized.

Figure 12A:
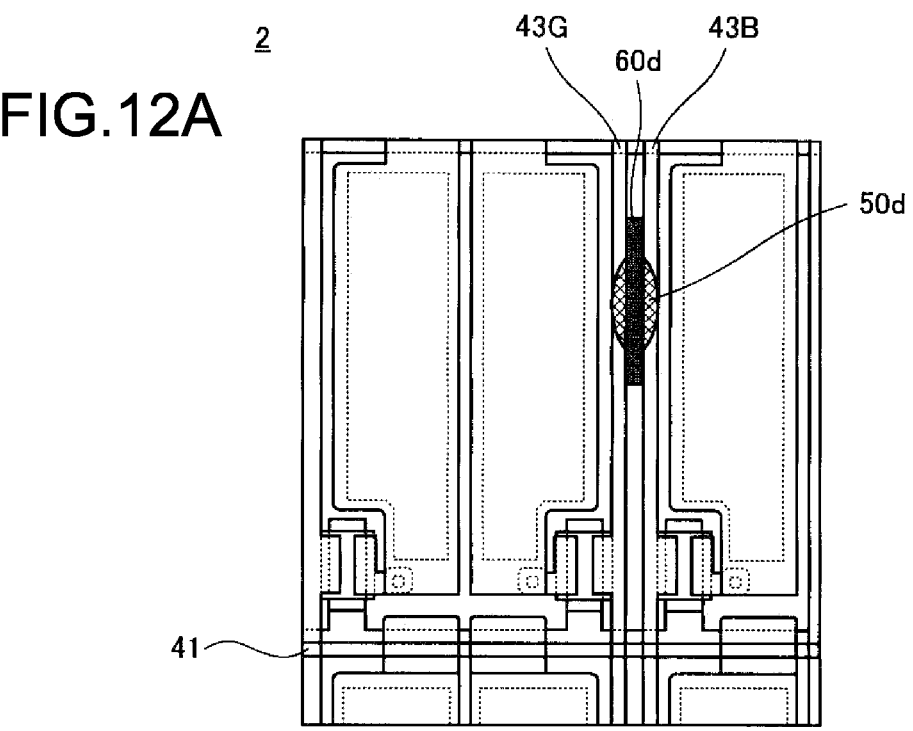
FIGS. 12A and 12B are diagrams showing a template that requires disconnection and a template that requires disconnection and connection, respectively.
Figure 12B:
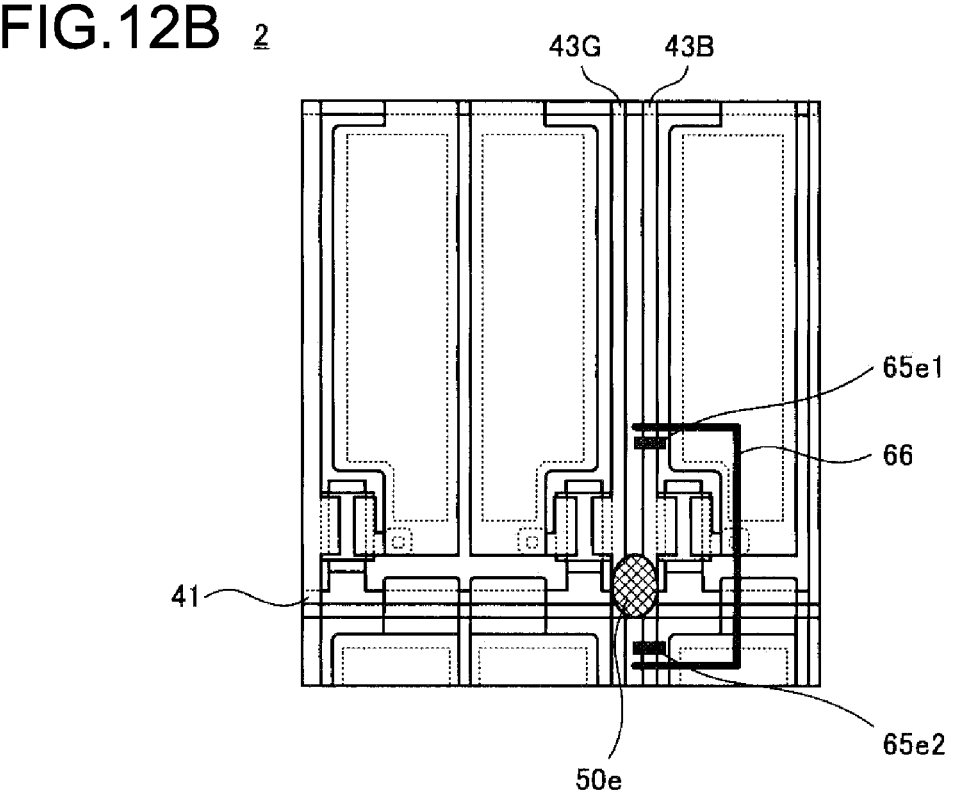

In the example of the defect shown in FIG. 9, two types of defect repair techniques as shown in FIGS. 12A and 12B have to be registered.

In a defect 50d shown in FIG. 12A, the potential supply wiring 43G and the potential supply wiring 43B of the wiring portion 2 are disconnected, thereby eliminating the short circuit. A template therefor includes a repair object 60d for disconnection.

A defect 50e shown in FIG. 12B short-circuits the potential supply wiring 43G and the potential supply wiring 43B of the wiring portion 2 and overlaps with the scanning wiring 41. In this case, another layer is disposed below the scanning wiring 41. Therefore, when the defect 50e is directly irradiated with laser light, the scanning wiring 41 on a lower layer may be undesirably disconnected. In other words, only by disconnecting an upper part and a lower part of the potential supply wiring 43B by using repair objects 65e1 and 65e2 and then connecting them by using a repair object 66 for connection, the short circuit can be eliminated.

Figure 13:
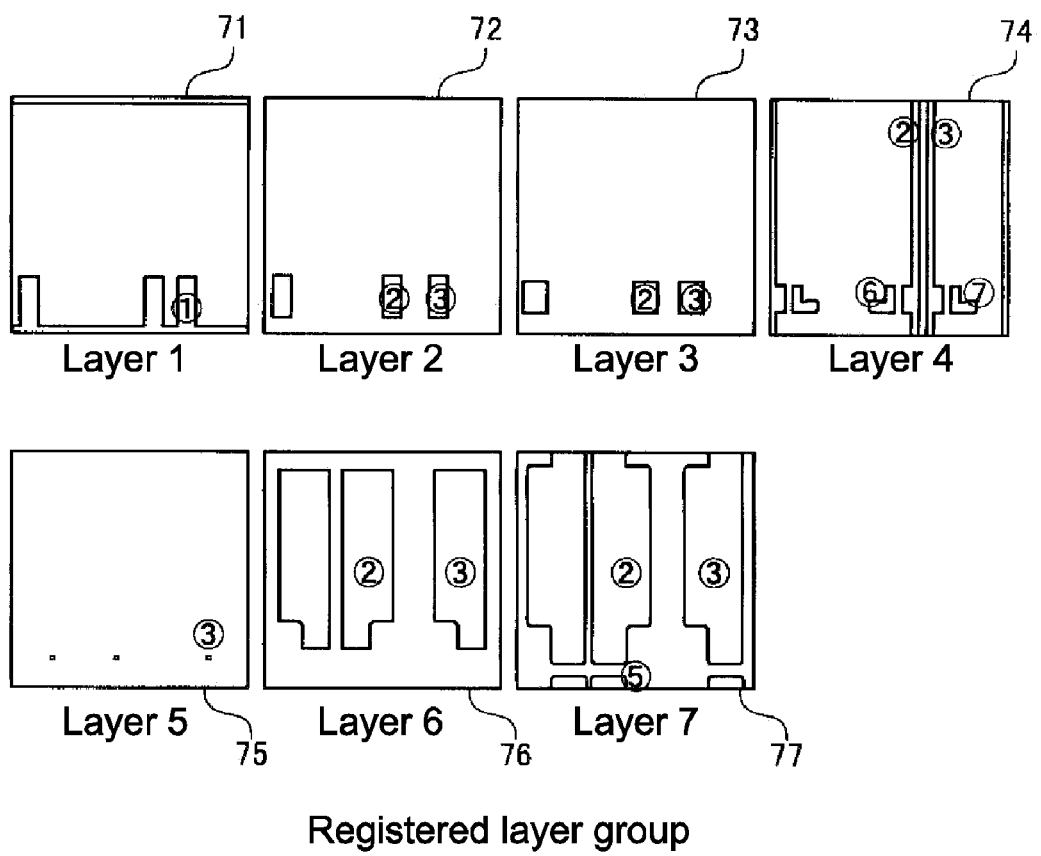
FIG. 13 is a diagram showing a layer structure of the wiring pattern shown in FIG. 11.

FIG. 13 is a diagram showing respective layers of the wiring pattern (wiring portion 2) shown in FIG. 11. In the figure, circled numbers in the layers each indicate a label ID of a label thereof.

In this example, the wiring portion 2 is constituted of seven layers 1 to 7 (images 71 to 77), for example. For each of the layers, as layer information, an order in which the layers are superposed (ID: identification information) and a layer name are set, and an ID is assigned to each individual area (label), thereby registering label information. The label indicates a part in a layer, in which specific areas or positions that correspond to members such as a wiring, an electrode, and a contact hole are provided as an individual area in the layer. The layer information include the identification information, attribute information, or the like of the layer, and can be obtained from design circuit information such as a CAD pattern or manual input information. The layer information and the label information are obtained while receiving the substrate 3 conveyed.

Figure 14:
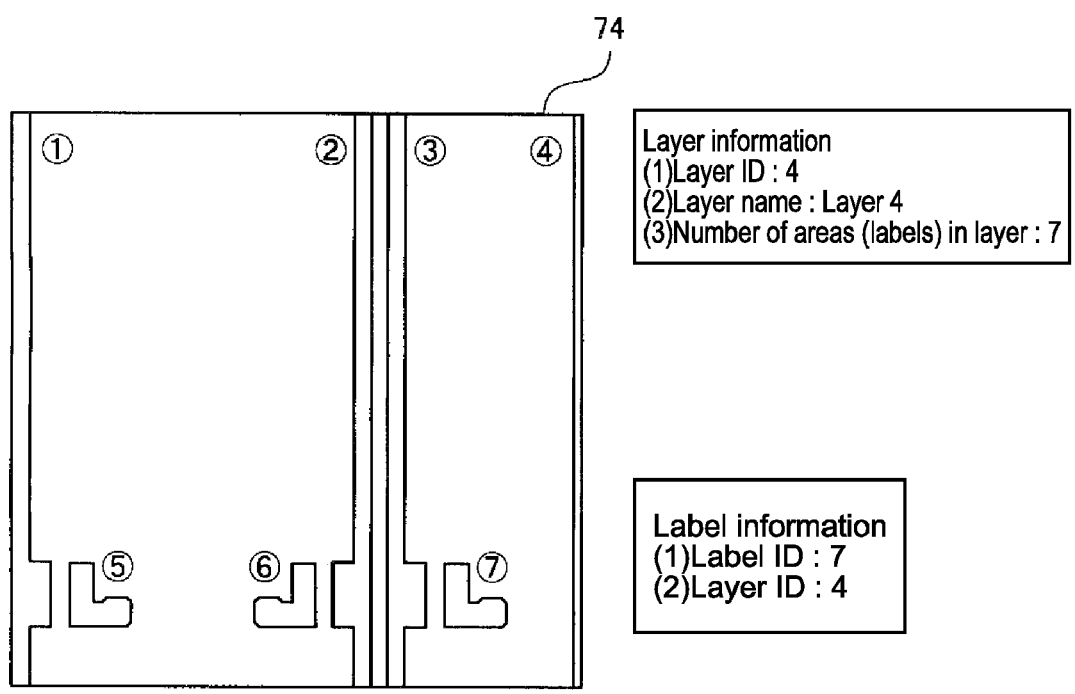
FIG. 14 is a diagram provided for an explanation of layer information and label information according to the first embodiment of the present invention.

FIG. 14 is a diagram showing the layer 4 (image 74) shown in FIG. 13. In the layer 4, seven labels are set.

In the layer information,
(1) the layer ID
(2) the layer name, and
(3) the number of areas (labels) in the layer are set.

In the layer 4 in this example, "(1) layer ID: 4", "(2) layer name: layer 4", and "(3) the number of areas (labels) in the layer: 7" are registered as the layer information.

Further, in the label information, for example,
(1) the label ID and
(2) the layer ID (to which the label belongs) are set.

In a label 7 in the layer 4 shown in FIG. 14, "(1) label ID: 7" and "(2) layer ID: 4" are registered as the label information.

Figure 15:
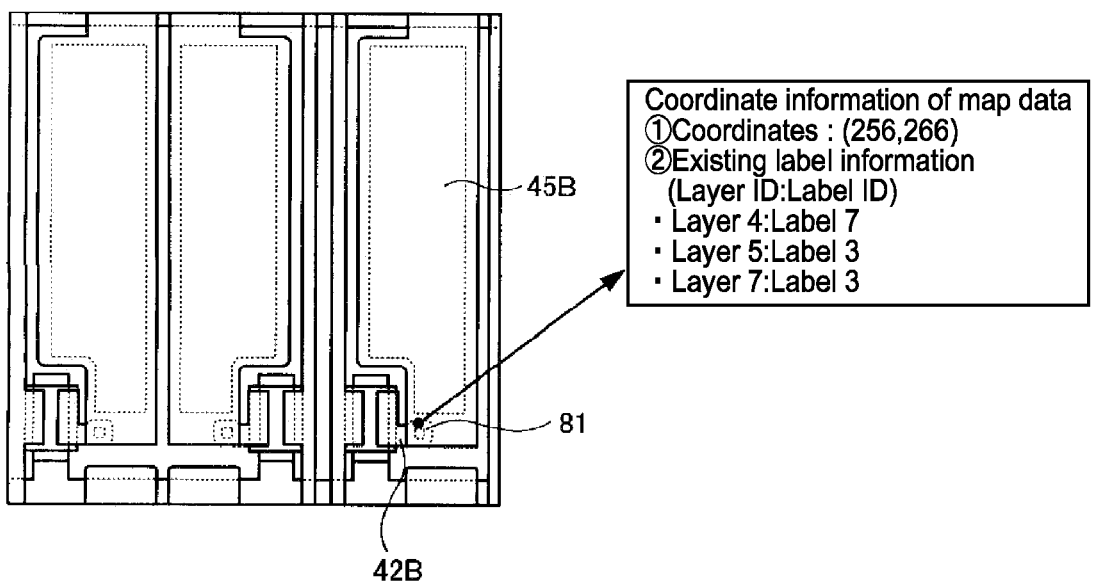
FIG. 15 is a diagram provided for an explanation of map data according to the first embodiment of the present invention.

Further, as shown in FIG. 15, information items of all the layers and labels that are registered are repetitively developed as coordinate values (relative coordinates with respect to the reference coordinates) in the pattern, thereby creating map data.

In the map data,
(1) the coordinates and
(2) existing label information (layer ID: label ID) are registered.

In a case of a point 81 shown in FIG. 15, from the layer group registered shown in FIG. 13, "(1) coordinates: (256, 266)" and "(2) existing label information: (layer 4: label 1), (layer 5: label 3), and (layer 7: label 3)" are registered, for example.

Figure 16:
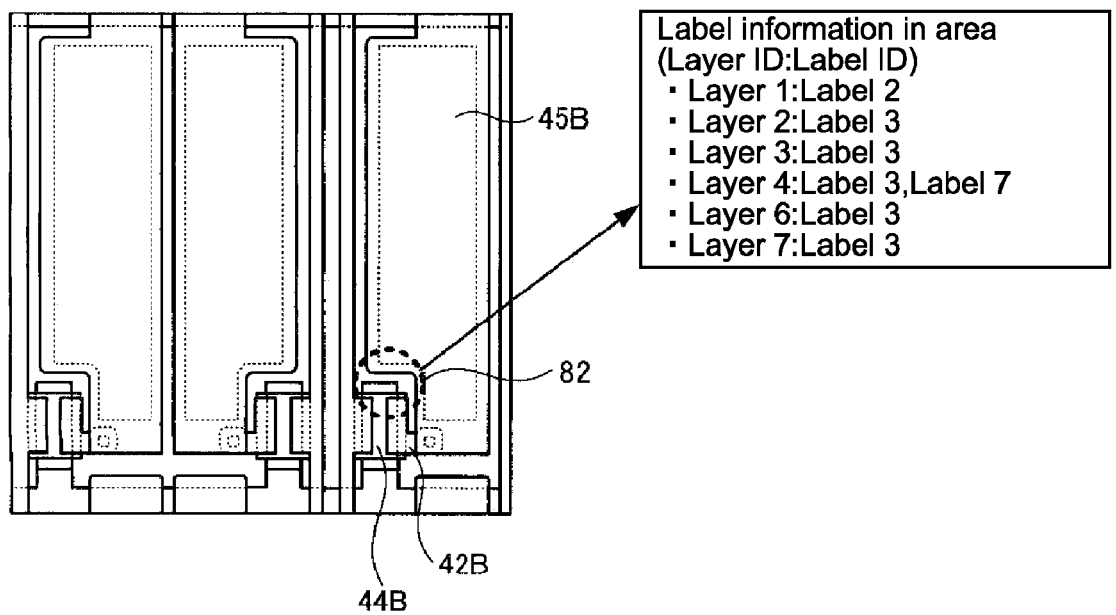
FIG. 16 is a diagram provided for an explanation of area information according to the first embodiment of the present invention.

FIG. 16 is a diagram showing an example in a case where area information of a specific range is obtained.

When the area information of the specific range is to be obtained, the coordinate information of the map data in the entire range to be obtained is scanned to obtain the area information as an output value. For example, in an area 82 shown in FIG. 16, from the layers registered shown in FIG. 13, "(layer 1: label 2), (layer 2: label 3), (layer 3: label 3), (layer 4: label 3, label 7), (layer 6: label 3), and (layer 7: label 3)" are output as the label information in the area.

Figure 17:
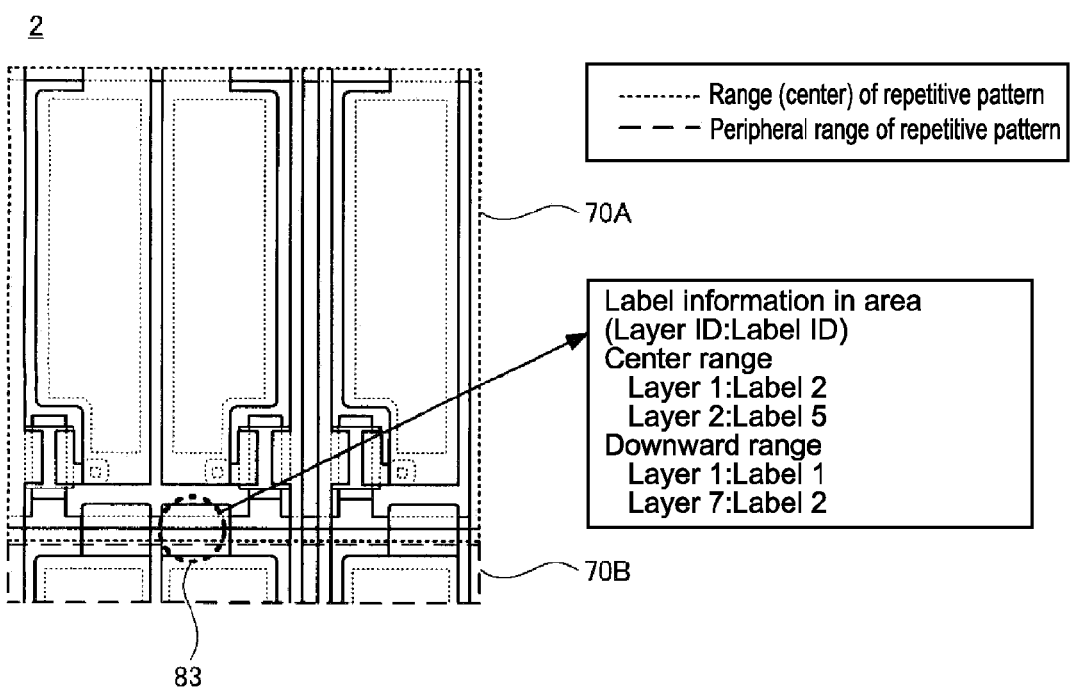
FIG. 17 is a diagram provided for an explanation of area information according to the first embodiment of the present invention.

FIG. 17 is a diagram showing an example in a case where area information of an area outside the repetitive pattern area is obtained.

When the area outside the repetitive pattern area, the area information thereof is obtained by shifting the map data in eight directions therearound in addition to a direction from the repetitive pattern area. Thus, for the area (defect) that overlaps with the plurality of repetitive patterns, the area information can also be set and obtained.

For example, a description will be given on a case of a defect 83 that overlaps with two repetitive patterns 70A and 70B as shown in FIG. 17. The repetitive pattern 70A is in the range of the repetitive pattern, that is, (the repetitive pattern of) a central range. On the other hand, the repetitive pattern 70B is in the range of the vicinity of the repetitive pattern 70A in the central range.

In this example, from the registered layer group shown in FIG. 13, "central range (layer 1: label 2), (layer 7: label 5), and downward range (layer 1: label 1), (layer 7: label 2)" are registered as the label information (layer ID: label ID) in the area.

Next, the area information of the map data is registered as additional information to the defect information registered in the template. For example, the area information items on the two types of templates shown in FIGS. 12A and 12B are as shown in FIGS. 18A and 18B.

Figure 18A:
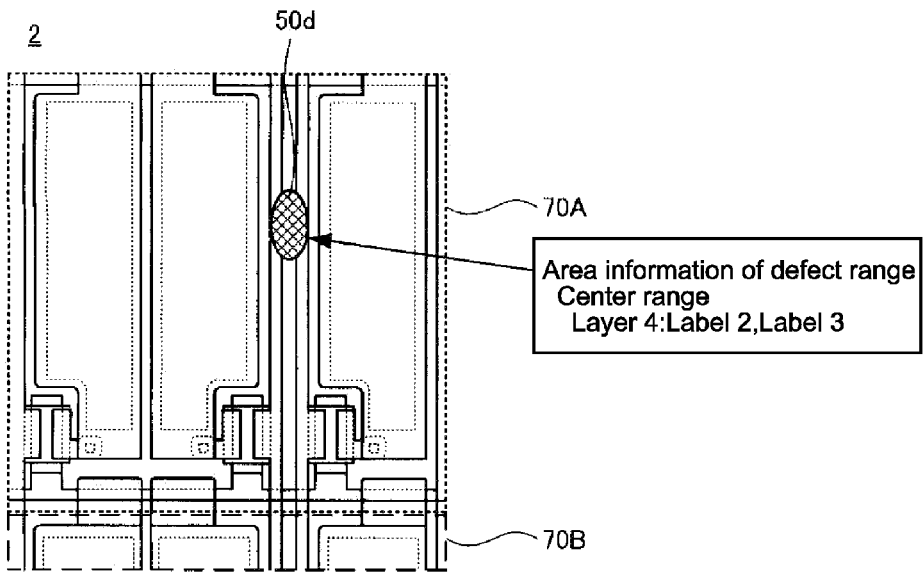
FIGS. 18A and 18B are diagrams for explaining area information of a first template according to the first embodiment of the present invention and for explaining area information of a second template according to the first embodiment of the present invention, respectively.
Figure 18B:
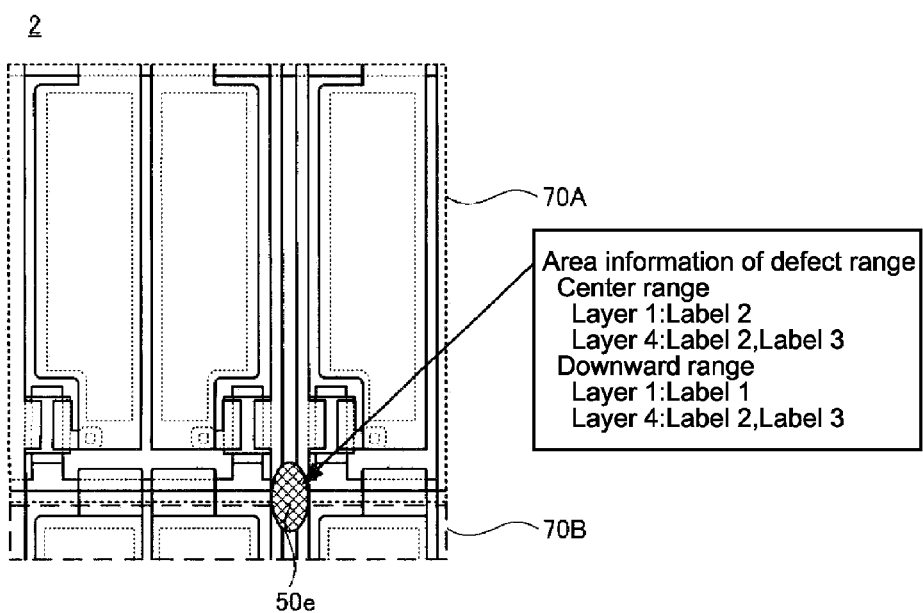

Regarding the defect 50d shown in FIG. 18A, from the registered layer group shown in FIG. 13, "central range (layer 4: label 2, label 3)" is registered as the area information of the defect range. Further, regarding the defect 50e shown in FIG. 18B, from the registered layer group shown in FIG. 13, "central range (layer 1: label 2), (layer 4: label 2, label 3), and downward range (layer 1: label 1), (layer 4: label 2, label 3)" are registered as the area information of the defect range.

For actually checking the defect with the template, the defect range is scanned (analyzed) in the same way as the template, and the area information that exists in the defect range is obtained, thereby performing comparison. For comparison, the following judgment conditions are defined and combined to determine the priority order.

(Regarding Area Match Rate and Area Mismatch Rate)

Next, a description will be given on a process performed by the area match rate/mismatch rate calculating unit 252.

The match rate and the mismatch rate of comparison information obtained when an actual defect range and a defect range that is supposed (set) by the template are compared with each other are defined as follows.

Area Match Rate:

The area match rate indicates a rate of area information of the template which is included in the defect area. When the number of defect area information items is represented by DefDataSize and the number of defect area information items included in the area information items of the template is represented by DefCompSize, the area match rate PerRank is expressed as follows.

PerRank=(DefCompSize/DefDataSize)*100

Area Mismatch Rate:

The area mismatch rate indicates a rate of template area information that is not included in the defect area information. When the number of template area information items is represented by TempDataSize and the number of defect area information items included in the template area information items is represented by DefCompSize, the area mismatch rate PerWas is expressed as follows.

PerWas=|((DefCompSize−TempDataSize)/TempDataSize)*100|

Area Match Threshold Value:

An area match threshold value is a threshold value of the area match rate, and is used as a determinant factor of a defect area judgment level of a next item in addition to the area match rate. As the match rate between the area structures of the template and the defect is higher, the output priority of the template is increased.

Area Mismatch Threshold Value:

An area mismatch threshold value is a threshold value of the area mismatch rate, and is used as a determinant factor of the defect area judgment level of the next item in addition to the area mismatch rate. As the match rate between the area structures of the template and the defect is higher, the output priority of the template is increased. When there are a large number of constituents that does not match between the area structures of the template and the defect, the output priority of the template is decreased.

Figure 19:
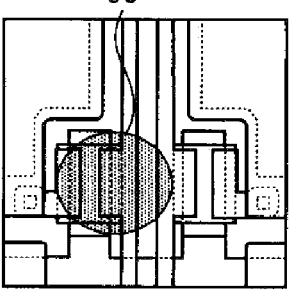
FIG. 19 is a diagram for explaining a match rate and a mismatch rate of defect areas according to the first embodiment of the present invention.
Figure 19:
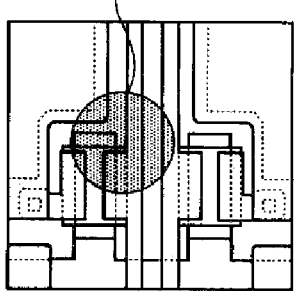

In an example shown in FIG. 19, the left figure shows the template, and the right figure shows the actual defect. In this case, the match rate of the defect area and the mismatch rate thereof are determined as follows.

Between a defect range 90 of the left template and a defect range 100 of the right actual defect, there are mismatch points in the layers 4, 6, and 7 (see, registered layer group shown in FIG. 13).

The number of defect area information items (DefDataSize): 7

The number of template area information items (TempDataSize): 6

The number of defect area information items that matches the template (DefCompSize): 5

Accordingly,

The area match rate (PerRank) and the mismatch rate (PerWas) are determined as follows.

PerRank=(DefCompSize/DefDataSize)*100≈71.4

PerWas=|((DefCompSize−TempDataSize)/TempDataSize)*100|≈16.6

(Regarding Defect Area Judgment Level)

Next, a description will be given on an operation by the defect area judgment level calculating unit 253.

The defect area judgment level is a judgment level of the comparison information obtained when the defect range is compared with the defect range that is set in the template based on the area match rate and the area mismatch rate described above. The judgment level is ranked as described below. As the judgment level is raised, the defect has a feature closer to that of the template.

Area judgment level S: Area structure information items that are compared match each other completely.

Area judgment level A: All defect area structure information items are included in template area structure information items, but there are a large number of the template area information items (label elements).

Area Judgment Level B:

(1) All the template area information items are included in the defect area structure information items, but there are a large number of defect area information items, or (2) the area match rate is higher than the area match threshold value, and the area mismatch rate is lower than the area mismatch threshold value (there is a possibility that a defect may be remained).

Area judgment level C: Some area structure information items that are compared match each other, but the match rate does not meet the standard of the area judgment level B (all the template area information items are not included and the standard of the threshold value is not met), and the template has some area information items that are not included in the defect area information items (there is a possibility that the position of the defect may not correspond to the actual defect position).

Area judgment level D: The area structure information items that are compared do not match at all (there is a possibility that the defect is different from that set in the template).

Figure 20:
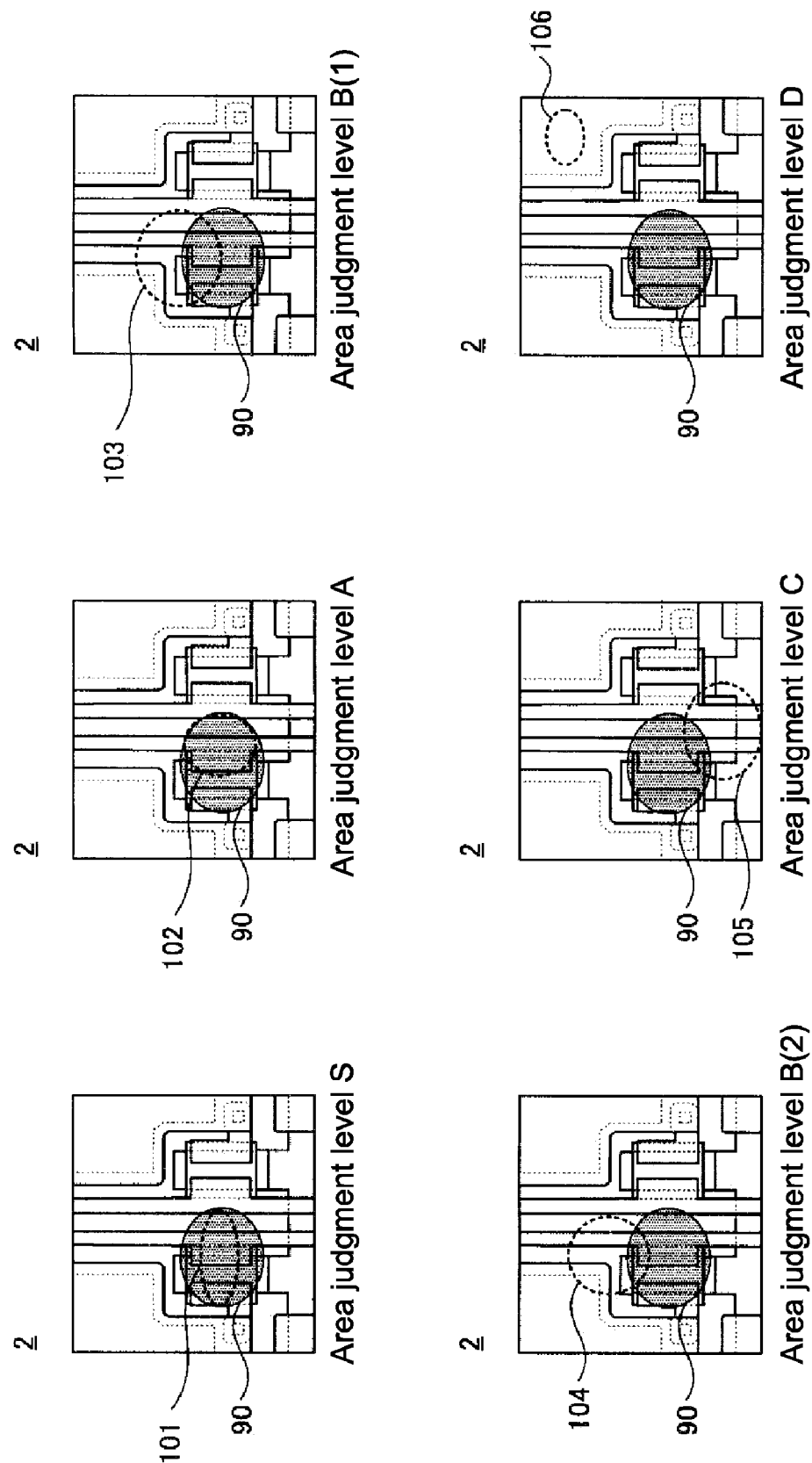
FIG. 20 is a diagram for explaining a defect area judgment level according to the first embodiment of the present invention.

FIG. 20 is a diagram showing (six) examples of the area judgment levels in a case where the area match threshold value is set to 70% and the area mismatch threshold value is set to 30%. It should be noted that in FIG. 20, the area match rate and the area mismatch threshold value are 71.4% and 16.6%, respectively, in the area judgment level B(2), and the area match rate and the area mismatch threshold value are 50% and 50%, respectively, in the area judgment level C.

In FIG. 20, the defect range 90 is an area set by the template (see, FIG. 19), and defect ranges 101 to 106 are actual defect areas.

Case of Defect Range 101:

The defect range 101 of the actual defect is included in the defect range 90 of the template, and the area structure information items that are compared match each other completely. Therefore, the area judgment level is determined to be "S".

Case of Defect Range 102:

The defect range 101 of the actual defect is included in the defect range 90 of the template, but the area judgment level is determined to be "A" based on the area match rate or the area mismatch rate.

Case of Defect Range 103:

The defect range 103 of the actual defect is overlapped with the defect range 90 of the template, and all the template area structure information items are included in the defect area structure information items. However, there are a large number of defect area structure information items, and therefore the area judgment level is determined to be "B(1)".

Case of Defect Range 104:

The defect range 104 of the actual defect is overlapped with the defect range 90 of the template, but the area match rate is higher than the area match threshold value and the area mismatch rate is lower than the area mismatch threshold value. Therefore, the area judgment level is determined to be "B(2)".

Case of Defect Range 105:

The position of the defect of the template is different from that of the actual defect. The area structure information items that are compared partly match each other, but the match rate does not meet the standard of the judgment level B and the template includes area information items that are not included in the defect area structure information items. Therefore, the area judgment level is determined to be "C".

Case of Defect Range 106:

The position of the defect of the template is completely different from that of the actual defect, and the area structure information items that are compared do not match at all. Therefore, the area judgment level is determined to be "D".

At the area judgment levels S and A out of the above-described defect area judgment levels, all the area structure information items of the defect are included in the area structure information items of the template, and the number of area information items (label elements) of the template is equal to or larger than that of the defect. Accordingly, at the area judgment levels S and A, the defect can be reliably repaired.

(Regarding Template Selection Judgment Level)

Next, a description will be given on a process by the template selection judgment level calculating unit 254.

The template selection judgment level sets match conditions of the area structure information items of the output template. The template selection judgment level is ranked as described below. As the judgment conditions are stricter, the detection rate is decreased, but the defect repair technique is considered to be more correct.

In addition, in selection judgment levels A and B, when there are a plurality of template candidates to be output, a template at a higher selection judgment level is preferentially output.

Selection Judgment Level S:

Templates other than those at the area judgment level S are excluded from the output candidates.

Selection Judgment Level A:

The templates to the area judgment level A are set as the output candidates. The defect is repaired, but an unnecessary repair process may be performed.

Selection Judgment Level B:

In a case where the area structure information items that are compared match in at least one point (to the area judgment level C), the template is set as the output candidate. The repair with respect to the defect is not completely ensured, but it may be possible to repair the defect depending on the way to set the template defect area registered.

(Regarding Template Output Judgment Level)

Next, a description will be given on a process by the template output judgment level calculating unit 255.

When a plurality of templates as the output candidates are detected based on the template selection judgment levels, the positional information items of the defects of the templates detected are compared to determine the priority order of the templates to be output. It should be noted that the output judgment levels in the following may be manually switched by the operator.

High Output Judgment Level:

As an overlapping area of the defect set in the template and the actual defect is larger, the template is preferentially output. Further, in a case where the template has no defect that overlaps with the actual defect, the template is deleted even when the selection judgment level of the template is determined to be "S".

Low Output Judgment Level:

A template having the defect in which coordinates of a gravity center thereof are close to those of the actual defect is preferentially output.

Figure 21:
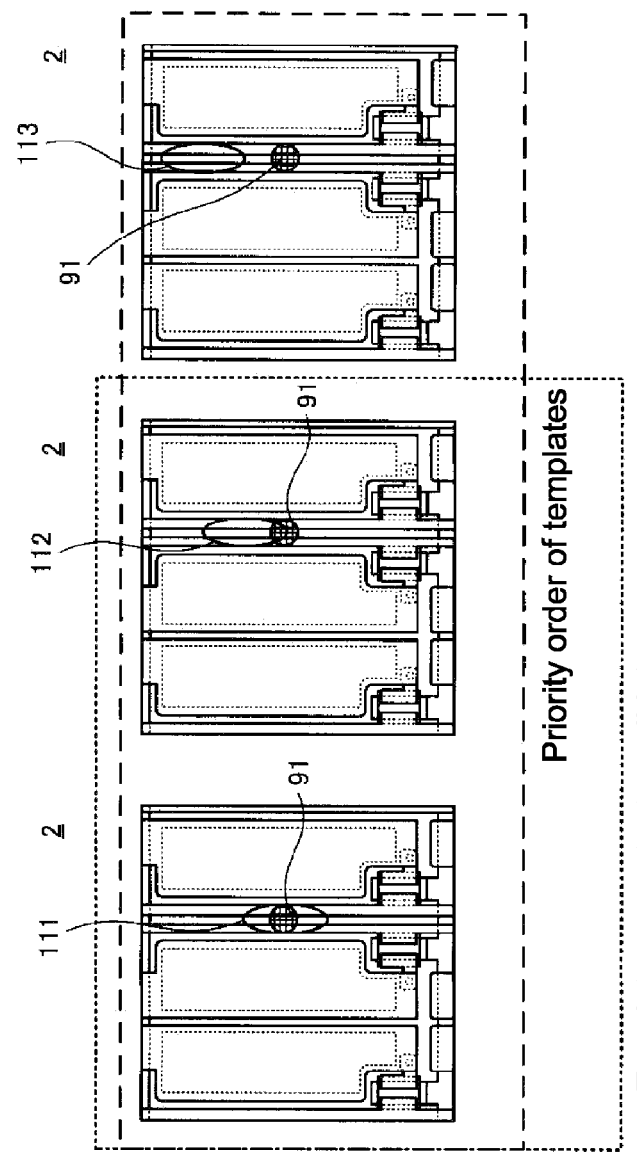
FIG. 21 is a diagram for explaining a template output judgment level according to the first embodiment of the present invention.
Figure 21:
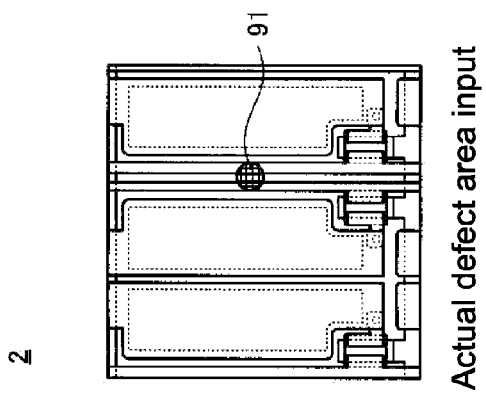

FIG. 21 is a diagram showing an example of determining the priority order when there are a plurality of templates at the same area judgment level in the case where the output judgment level is high.

In this example, three templates are selected with respect to an area of an actual defect 91 which is input. Defects 111, 112, and 113 set in the respective templates are deviated from the area of the actual defect by a larger distance and have smaller areas that overlap with the actual defect in the stated order. In this case, the priority is given to the templates in the order of the template including the defect 111, the template including the detect 112, and the template including the defect 113, and the output judgment level is high. Therefore, the templates including the defect 111 and the defect 112 are respectively determined to be the output candidates. That is, even if the area judgment level is high, when the defect set in the template does not overlap with the actual defect, the priority order of the template is decreased.

As described above, in the case where the output judgment level is set to be high, even when the defect of the template is close to the actual defect, the template is deleted if the defect thereof does not overlap with the actual defect. This is effective for a case where the positions of defects registered in the template are finely set to minimize the number of repair points (FIG. 22), a case where the defect area is broadly defined and the defects to be repaired are shared to minimize the number of templates registered (FIG. 23), and a case where the area which is supposed to include the defect is highly difficult to be repaired (FIG. 24).

Figure 22:
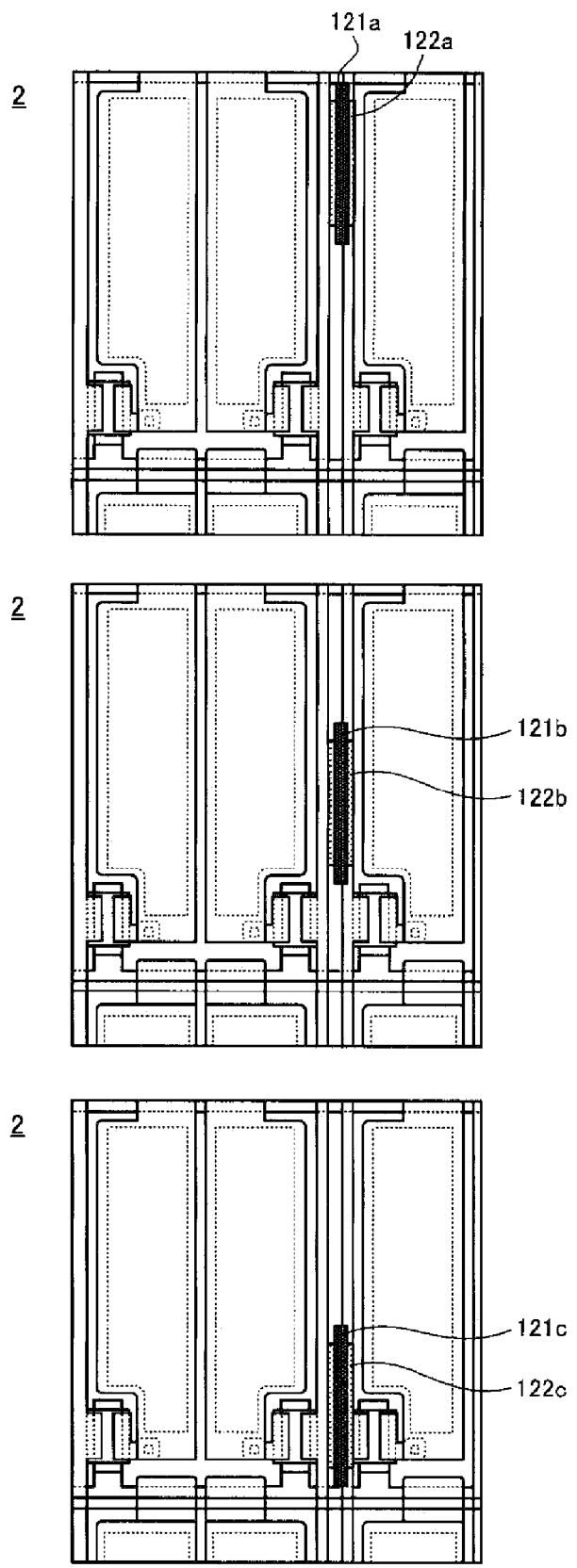
FIG. 22 is a diagram showing examples (1) of the templates that are effective in a case where the template output judgment level is high according to the first embodiment of the present invention.

FIG. 22 (upper, middle, and lower diagrams) shows three templates in which defects 121*a*, 121*b*, and 121*c* (defect objects) are set at appropriate positions with respect to defects 122*a*, 122*b*, and 122*c* that have the same area information but are generated at the different positions, respectively.

Figure 23:
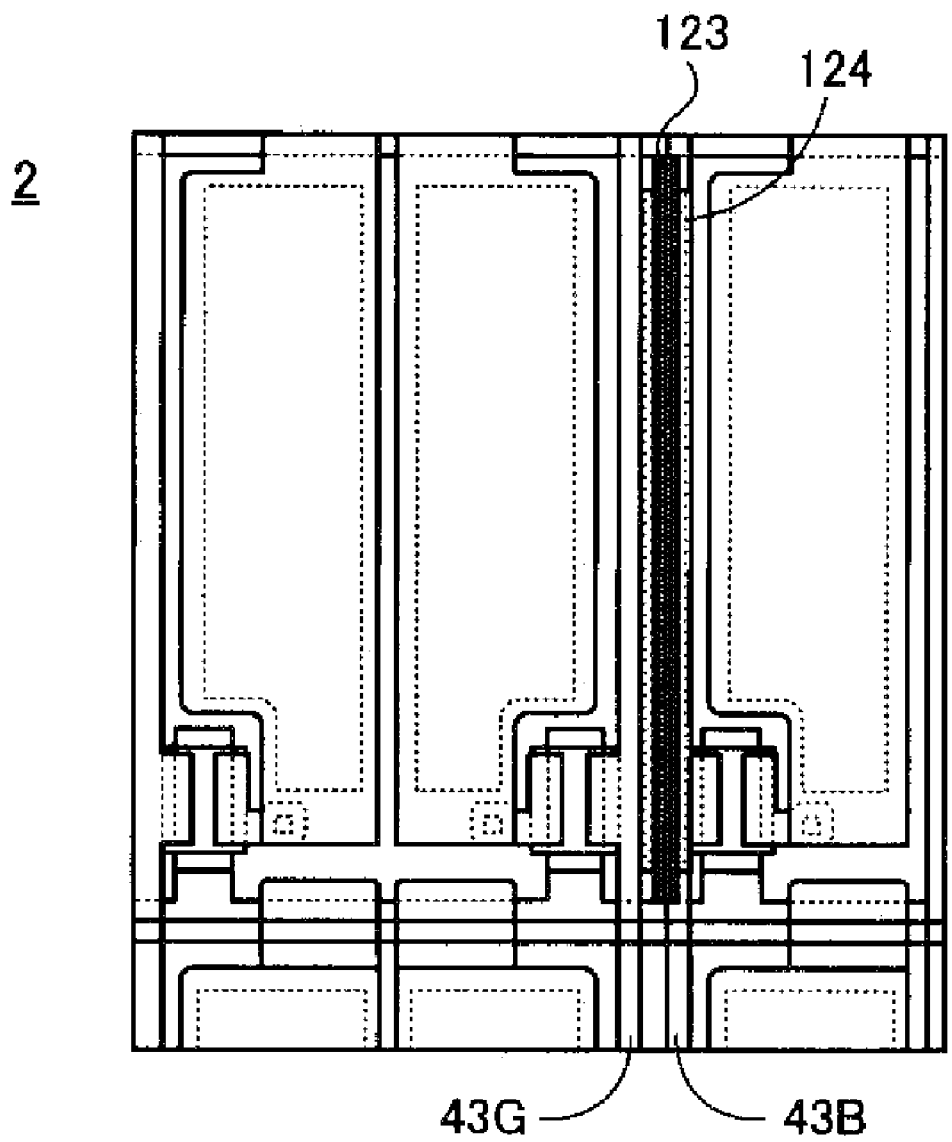
FIG. 23 is a diagram showing examples (2) of the templates that are effective in a case where the template output judgment level is high according to the first embodiment of the present invention.

In the template shown in FIG. 23, a defect 123 (defect object) formed to be long so as to correspond to a long defect 124 having a shape like linked three defects shown in FIG. 22 is set. It should be noted that when a large defect range is registered, the match rate with the actual defect is decreased. As the defect range registered is smaller, the match rate with the actual defect is increased.

Figure 24:
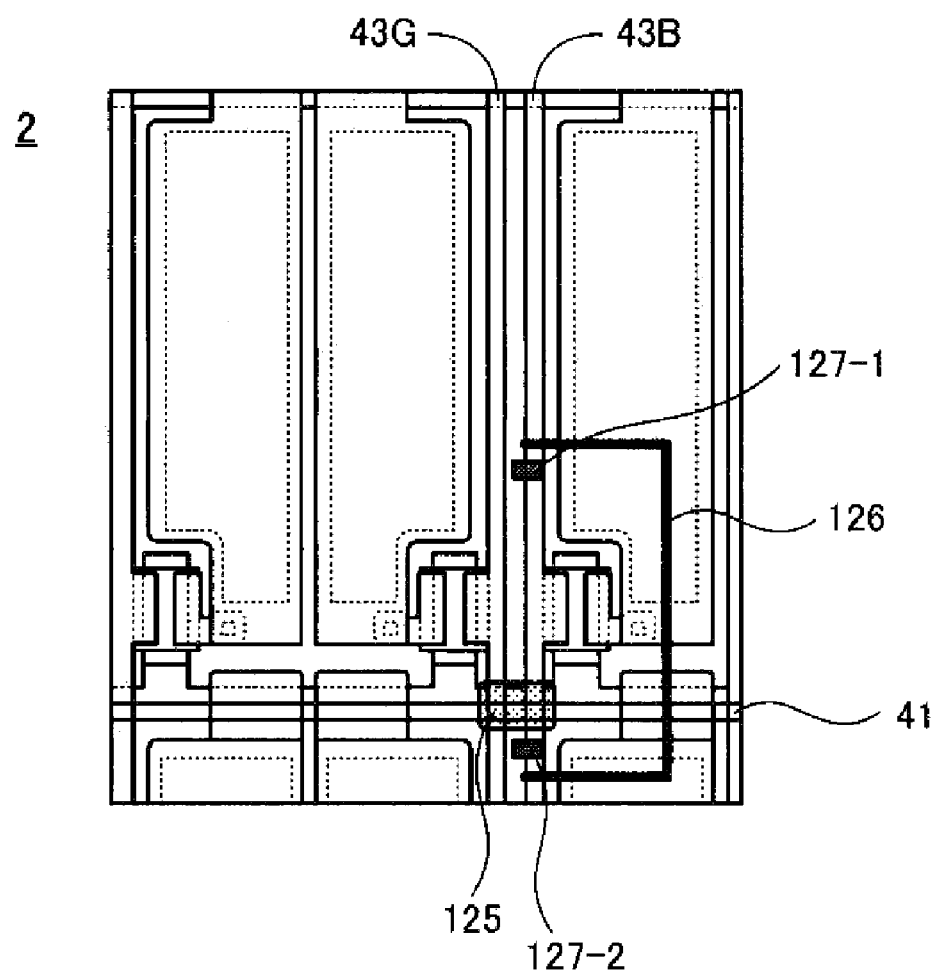
FIG. 24 is a diagram showing examples (3) of the templates that are effective in a case where the template output judgment level is high according to the first embodiment of the present invention.

A defect 125 shown in FIG. 24 overlaps with the scanning wiring 41 and the potential supply wiring 43B and 43G, and lies in an area that is difficult to be repaired and should be treated carefully (see, FIG. 12). In this case, a layer structure is taken into consideration in addition to the position and the size of the defect. As a result, defect objects 127-1 and 127-2 for disconnection and a defect object 126 for connection select templates that are set, thereby making it possible to perform appropriate repair without damaging the wiring pattern.

In addition, in the case where the output judgment level is low, it is effective when one defect repair technique can be applied to a broad range or when the position of the defect can be determined.

Figure 25:
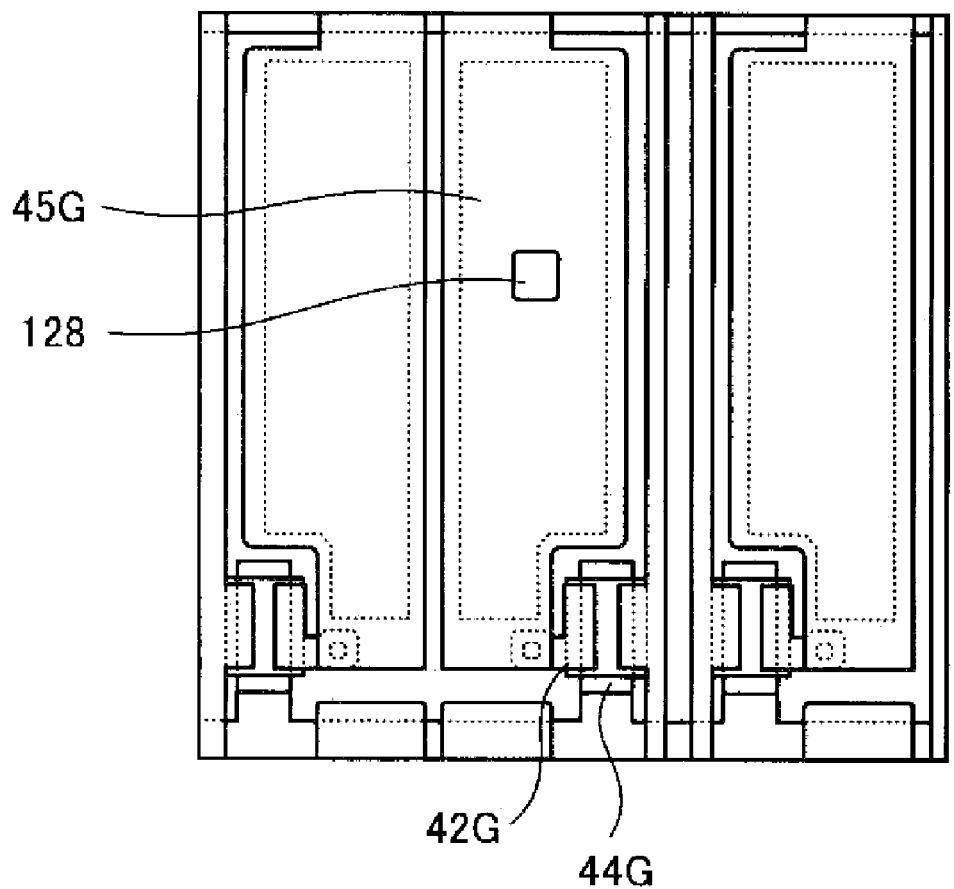
FIG. 25 is a diagram showing an example of a template that is effective in a case where the template output judgment level is low according to the first embodiment of the present invention.

In an example shown in FIG. 25, a defect 128 lies in the capacitor 45G. In this example, the defect 128 completely lies in a specific layer area, and the layer structure can be easily specified. Therefore, the need for complicate output judgment levels is reduced.

Further, in the case where the output judgment level is low, all the templates are selected in order of distance from the coordinates of the gravity center of the defect. It is also possible to select, from those templates, a template whose priority order is high under another condition. Alternatively, it is also possible to perform the repair while the operator checks a corresponding template that is displayed on the display 227, that is, while the operator consults the template as a dictionary.

According to the above embodiment, the registered area information structured in the repetitive pattern registered is defined, and the area information items (constituents) are compared between the actual defect and the defect repair technique (template), with the result that an optimal defect repair technique can be automatically selected from the registered defect repair techniques and performed.

In addition, by deleting an inappropriate defect repair technique even when the registered defect repair technique matches the defect in terms of an electrical definition, the defect repair technique is prevented from being erroneously detected, and the appropriate defect repair technique can be output.

Further, even when there are a plurality of defect repair techniques for a specific defect, by registering the area information in the defect range and comparing it with the area information of the template, it is possible to select the optimal defect repair technique in order of priority from the defect repair techniques for the defects which are electrically the same. As a result, the accuracy of the defect repair is improved.

That is, in the embodiment of the present invention, it is of course possible that specific circuit information in the substrate is used. But, the embodiment of the present invention specializes in the unique area judgment, which is optimal for the defect repair technique by setting the arbitrary area in the wiring portion, in addition to the circuit information and superficial defect information.

2. MODIFIED EXAMPLES

First Modified Example

Equipotential Area and Combined Area

Figure 26:
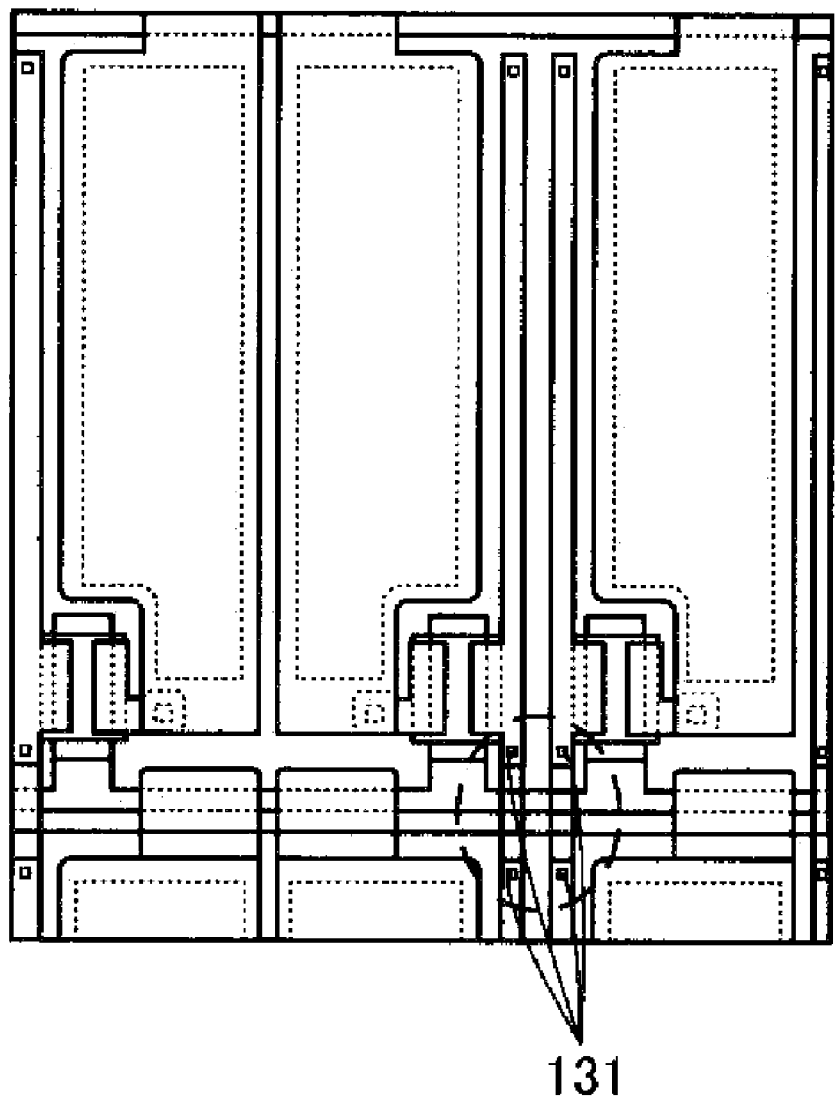
FIG. 26 is a diagram showing an example of the wiring pattern in a case where another layer is connected to be equipotential.

FIG. 26 is a pattern diagram of a repetitive pattern area in which a plurality of wiring patterns are formed on the substrate 3, which is different from FIG. 11 in that different layers (e.g., layer 4 and another layer) are connected through a contact hole 131 or the like to form an equipotential surface.

Figure 27:
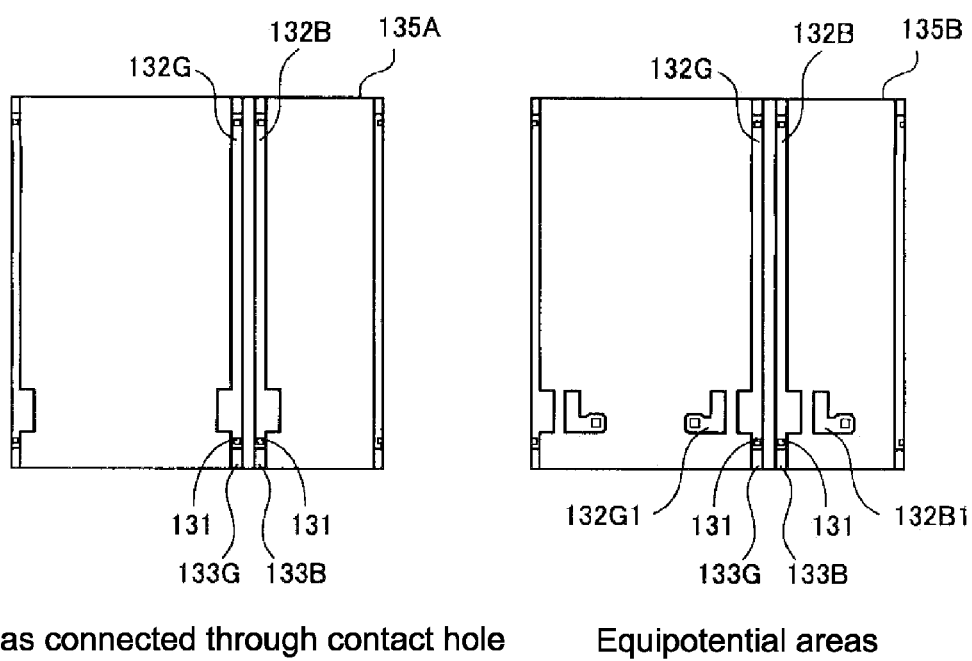
FIG. 27 is a diagram showing parts of layers forming the wiring pattern shown in FIG. 26.

In FIG. 27, the left diagram shows an example of a layer (image 135A) illustrated based on the layer 4 (image 74; see, FIG. 13). In this example, the potential supply wiring is indicated by an area in which wirings 132G and 132B of the layer 4 and wirings 133G and 133B of another layer are connected to each other through the contact hole 131.

On the other hand, in FIG. 27, the right diagram shows an example of a layer (image 135B) illustrated based on the layer 4 (image 74; see, FIG. 13). In this example, the wirings 132G and 132B of the layer 4 and the wirings 133G and 133B of the another layer are connected to each other through the contact hole 131, with the result that an equipotential area is obtained. Wirings 132G1 and 132B1 respectively disposed so as to be opposed to the wirings 132G and 132B that constitute the potential supply wiring are equipotential.

Figure 28:
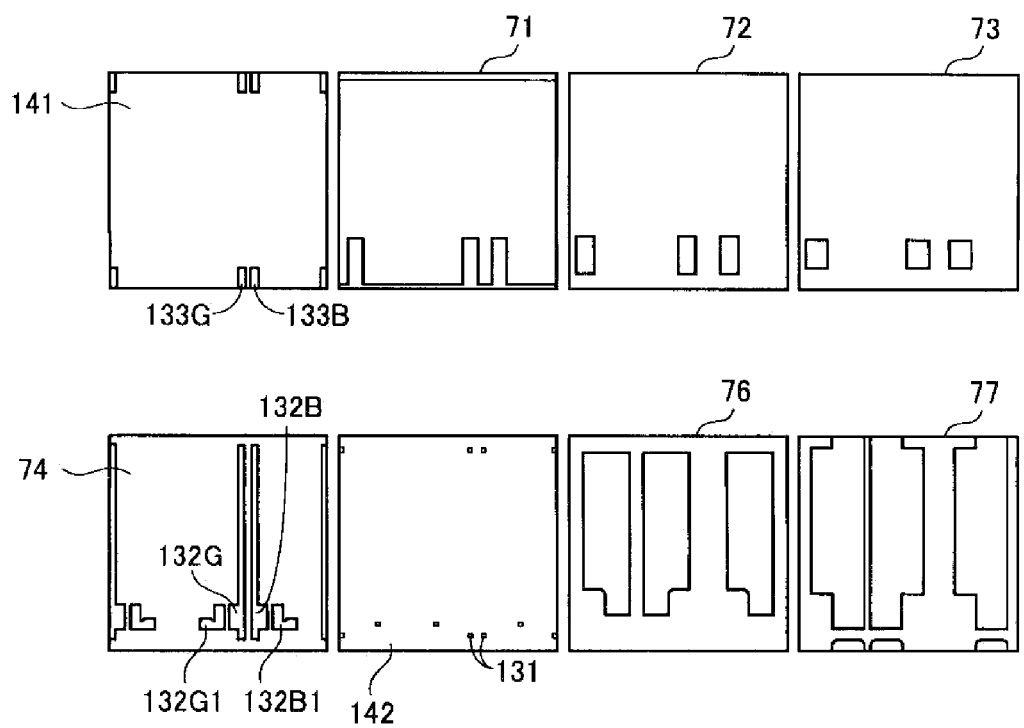
FIG. 28 is a diagram showing a layer structure of the wiring pattern shown in FIG. 26.

FIG. 28 is a diagram showing a layer structure (registered layer group) of the wiring portion 2 which corresponds to the examples shown in FIGS. 26 and 27.

In the examples, unlike the layer structure shown in FIG. 13, a layer including the wirings 133G and 133B (image 141) is added. In addition, in place of the layer 5 (image 75; see, FIG. 13), a layer (image 142) in which the contact hole 131 is formed is added.

In a case of the wiring pattern, an area obtained by combining specific layers is registered as an area for judgment, or an equipotential area is replaced with an existing layer to be registered, with the result that retrieval of the map data can be simplified and the data area can be reduced. The registered layer group shown in FIG. 28 is obtained by registering the area connected through the contact hole shown in the right diagram of FIG. 29 (area obtained by combining the specific labels) as the area for judgment in addition to the existing layer group shown in FIG. 13.

Figure 29:
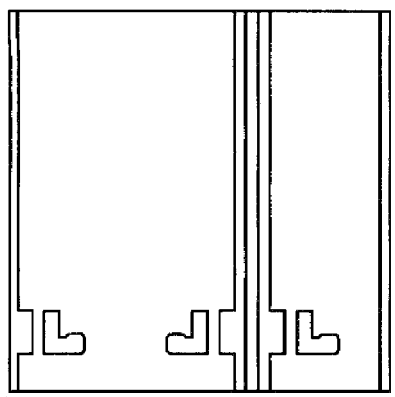
FIG. 29 is a diagram showing layer structure including an area formed by combining specific layers according to the first embodiment of the present invention.
Figure 29:
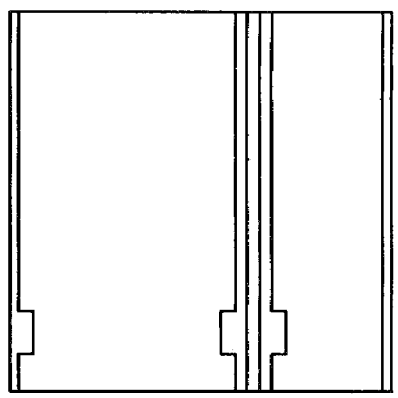
Figure 30:
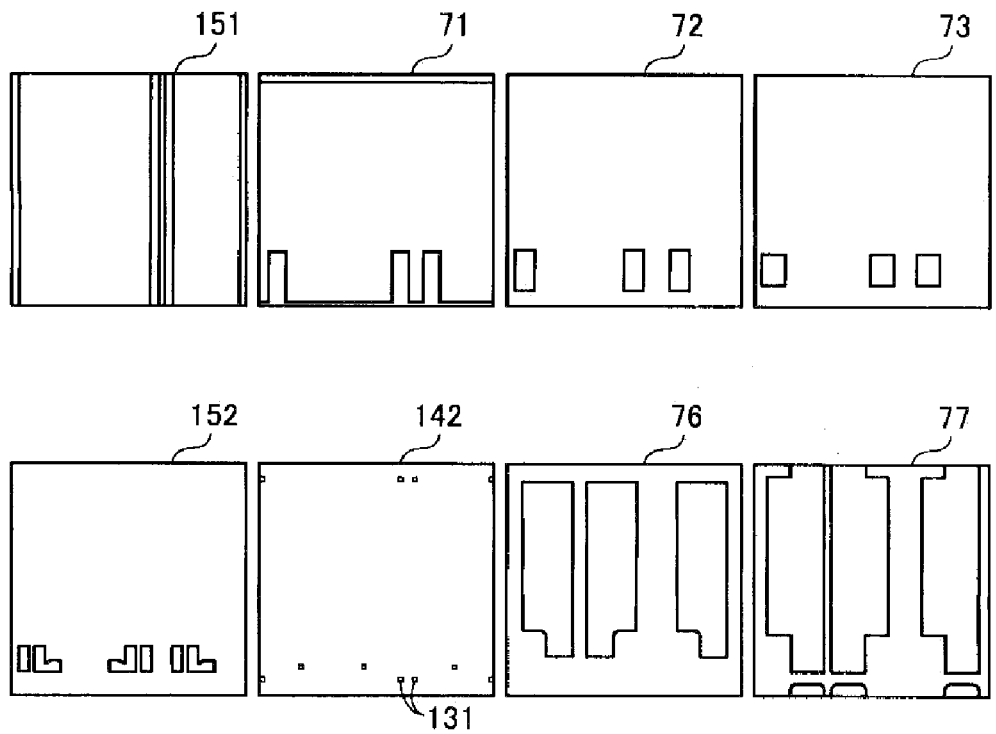
FIG. 30 is a diagram showing a layer structure including an area formed by replacing an area in the layer according to the first embodiment of the present invention.

FIG. 30 is a diagram showing a registered layer group in place of the area in the existing layer shown in FIG. 13 based on the equipotential area shown in the left diagram of FIG. 29.

Second Modified Example

Specification of Arbitrary Area

Figure 31:
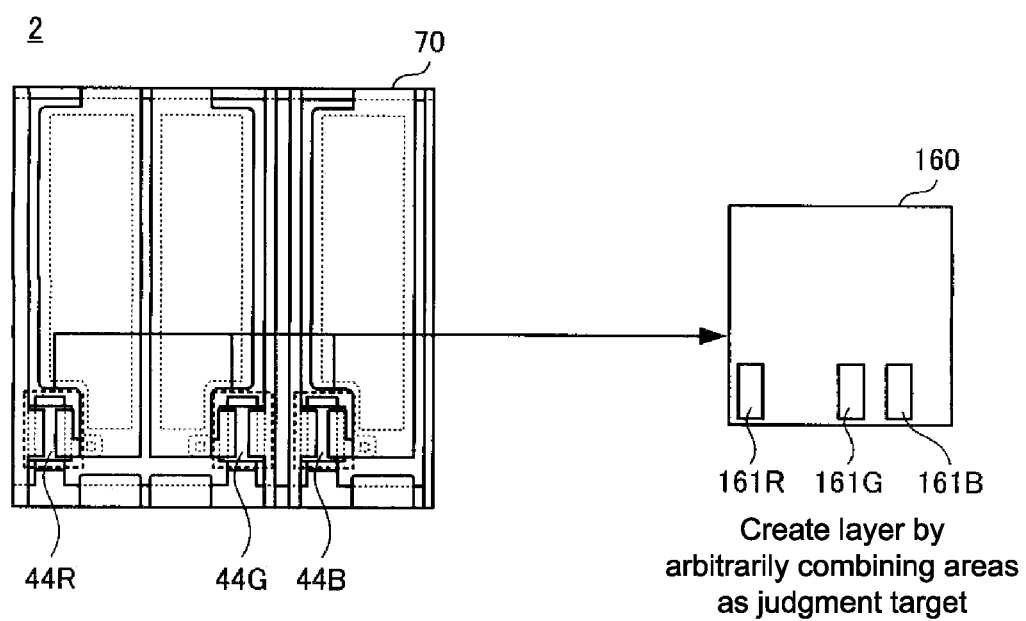
FIG. 31 is a diagram provided for an explanation of the layer formed by arbitrarily selecting a specific area according to the first embodiment of the present invention.
Figure 32:
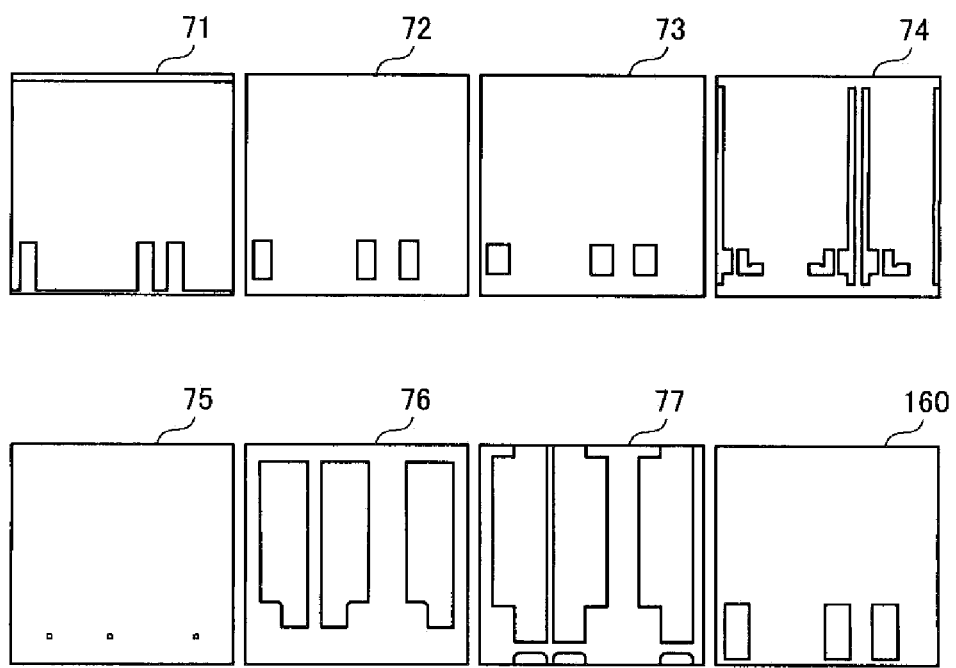
FIG. 32 is a diagram showing a layer structure of a wiring pattern to which a layer shown in FIG. 31 is added according to the first embodiment of the present invention.

FIG. 31 is a diagram showing an example in which specific areas are arbitrarily selected. That is, the TFT elements 44R, 44G, and 44B are selected from the image 70 of the wiring portion 2 and new area 161R, 161G, and 161B are registered, thereby forming a layer 160. FIG. 32 shows a state in which the layer 160 additionally formed is added to the existing layer structure shown in FIG. 13.

The layer is used for registering, in specific coordinates, information on the existence/nonexistence of the arbitrary area, and therefore it is also possible to perform judgment of the area without depending on design information of a circuit. Accordingly, areas of specific components in the wiring pattern are combined and a unique area for the defect repair is set for the judgment, with the result that the detection accuracy of the template can be improved. Further, it is possible to retrieve a template by using, as a substitute, an image obtained by capturing an area obtainable from an actual image in a case where there is no circuit information.

The embodiment described above is a specific example of the preferred embodiment for carrying out the present invention, and therefore various limitations that are technically desirable are imposed. However, the present invention is not limited to the above embodiment as long as the above embodiment does not include the description of particularly limiting the present invention. Accordingly, for example, the material used and the amount used therefor, the process time, the process sequence, the numeric conditions of the various parameters, and the like used in the above description are merely desirable examples. Further, the dimensions, the size, the positional relationships, and the like in the figures used in the above description are schematic and merely examples of the embodiment. The present invention is not limited to the above embodiment, and can be variously changed or modified without departing from the gist of the present invention.

In addition, in the above embodiment, the description is given on the case where the defect repair is performed on the design pattern formed on the glass substrate of the flat panel display, but the repair target is not limited to this example. For example, the defect repair according to the present invention can be applied to a predetermined pattern formed on a substrate as a repair target such as a semiconductor wafer, a photo mask, and a magnetic disk.

The control unit 201 shown in FIG. 6 implements the intended function by executing the program recorded on the non-volatile memory by the processing unit such as the MPU. Alternatively, the function blocks shown in FIG. 6 may be implemented by using individual programs. In addition, a plurality of functional blocks may be implemented by one program. Further, the function blocks shown in FIG. 6 may be implemented by using hardware.

In addition, the repair technique database 225 may be provided not in the defect repair apparatus 200, but in a remote server. By accessing the repair technique database 225 via a network such as a LAN and the Internet, the defect repair technique may be obtained.

The present application contains subject matter related to that disclosed in Japanese Priority Patent Application JP 2008-272528 filed in the Japan Patent Office on Oct. 22, 2008, the entire content of which is hereby incorporated by reference.

What is claimed is:

1. A defect repair apparatus, comprising:
   a defect detection unit operable to (i) inspect a multilayer substrate on which a repetitive pattern is formed (ii) extract positional information of a defect in the repetitive pattern, and (iii) extract feature information of the defect;
   a database operable to register a plurality of defect repair techniques;
   a defect repair unit operable to repair the defect of the multilayer substrate using one of the plurality of defect repair techniques; and
   a control unit operable to (i) read the one of the plurality of defect repair techniques for repairing the defect detected by the defect detection unit from the database based on a layer structure of the multilayer substrate, and (ii) control the defect repair unit that repairs the defect by using the one of the plurality of defect repair techniques, wherein,
      the database contains (i) layer information for individual layers of the multilayer substrate, and (ii) label information for individual areas of each of the individual layers.

2. The defect repair apparatus according to claim 1, wherein the control unit is configured to (i) compare area information of an actual defect with pre-registered area information corresponding to the defect in the repetitive pattern, and (ii) read the defect repair technique from the database based on a result of the comparison.

3. The defect repair apparatus according to claim 2, wherein at least one of the area information and the pre-registered area information include the layer information and the label information.

4. The defect repair apparatus according to claim 3, wherein:
   the layer information includes a layer ID that indicates at least one of an order of layers, a layer name, and a label count in the layer, and
   the label information includes a label ID for identifying a label in the layer and a layer ID that indicates a layer including the label.

5. The defect repair apparatus according to claim 4, wherein the database has map data based on the layer information and the label information, the map data including coordinate values in the repetitive pattern.

6. The defect repair apparatus according to claim 5, wherein the control unit includes,
   an area information obtaining unit operable to obtain the area information of the defect,
   an area match and mismatch rate calculating unit operable to calculate an area match rate and an area mismatch rate between the first area information obtained by the area information obtaining unit and the pre-registered area information in the repetitive pattern,
   a defect area judgment level calculating unit operable to judge, based on a predetermined threshold value, levels of the area match rate and the area mismatch rate that are calculated by the area match and mismatch rate calculating unit,
   a template selection judgment level calculating unit operable to select templates that indicate defect repair techniques based on a result of the judgment by the defect area judgment level calculating unit,
   a template output judgment level calculating unit operable to determine, based on a predetermined judgment level, an output priority order of the templates selected by the template selection judgment level calculating unit, and
   a defect repair executing unit operable to control the defect repair unit by using the defect repair technique based on the output priority order determined by the template output judgment level calculating unit.

7. A defect repair method, comprising:
   a first step of (i) inspecting a multilayer substrate on which a repetitive pattern is formed, (ii) extracting positional information on a defect in the repetitive pattern, and (iii) extracting feature information of the defect;
   a second step of reading a defect repair technique for repairing the defect detected in the first step from a database based on a layer structure of the multilayer substrate; and
   a third step of controlling a defect repair unit to repair the defect using the defect repair technique read in the second step,
   wherein,
      the database contains (i) layer information for individual layers of the multilayer substrate, and (ii) label information for individual areas of each of the individual layers.

8. The defect repair method of claim 7, wherein:
   the layer information includes a layer ID that indicates at least one of an order of layers, a layer name, and a label count in the layer, and
   the label information includes a label ID for identifying a label in the layer and a layer ID that indicates a layer including the label.

9. The defect repair method of claim 8, wherein the database has map data based on the layer information and the label information, the map data including coordinate values in the repetitive pattern.

* * * * *